United States Patent
Song et al.

(10) Patent No.: US 11,899,012 B2
(45) Date of Patent: Feb. 13, 2024

(54) SINGLE-CHAIN POLYMER-BASED TARGET RECEPTORS FOR USE IN ELECTROCHEMICAL DETECTION OF TARGET ANALYTES

(71) Applicant: University of New Hampshire, Durham, NH (US)

(72) Inventors: Edward Song, Durham, NH (US); William Rudolf Seitz, Durham, NH (US); Jeffrey M. Halpern, Durham, NH (US)

(73) Assignee: University of New Hampshire, Durham, NH (US)

( * ) Notice: Subject to any disclaimer, the term of this patent is extended or adjusted under 35 U.S.C. 154(b) by 0 days.

(21) Appl. No.: 18/149,131

(22) Filed: Jan. 2, 2023

(65) Prior Publication Data

US 2023/0152310 A1 May 18, 2023

Related U.S. Application Data

(63) Continuation of application No. 16/898,836, filed on Jun. 11, 2020, now Pat. No. 11,592,443.

(60) Provisional application No. 62/859,900, filed on Jun. 11, 2019.

(51) Int. Cl.
*G01N 33/543* (2006.01)
*G01N 33/553* (2006.01)
*G01N 33/68* (2006.01)
*G01N 27/327* (2006.01)

(52) U.S. Cl.
CPC ..... *G01N 33/5438* (2013.01); *G01N 27/3277* (2013.01); *G01N 33/553* (2013.01); *G01N 33/6812* (2013.01); *G01N 2600/00* (2013.01)

(58) Field of Classification Search
None
See application file for complete search history.

(56) References Cited

PUBLICATIONS

Al, Lunhong, et al., "Catalytic reduction of 4-nitrophenol by silver nanoparticles stabilized on environmentally benign macroscopic biopolymer hydrogel." Bioresource Technology 132 (2013) 374-377.

Arroyo Curras, N., et al., "Real-time measurement of small molecules directly in awake, ambulatory animals." Proc. Natl. Acad Sci., vol. 114, No. 4, pp. 645-650, Jan. 2017.

Boyer, C., et al., "One-pot synthesis and biofunctionalization of glycopolymers via RAFT polymerization and thiol-ebe reactions." Chem. Commun., pp. 6029-6031, Oct. 2009.

Burke, L.D., et al., "The electrochemistry of gold: I. The redox behaviour of the metal in aqueous media." Gold Bull., vol. 30, No. 2, pp. 43-53, Jun. 1997.

(Continued)

*Primary Examiner* — J. Christopher Ball
(74) *Attorney, Agent, or Firm* — Pierce Atwood LLP

(57) ABSTRACT

The present disclosure provides new approaches in developing templated polymer-based chemical receptors. At least some embodiments of the invention use a stimuli-responsive polymer [e.g., poly-Nisopropylacrylamide (pNIPAM)] as a polymer backbone with the incorporation of functional monomers (for analyte recognition). In at least some embodiments of the invention, vinylferrocene may be used as a redox-active label for electrochemical transduction.

19 Claims, 11 Drawing Sheets

(56) References Cited

PUBLICATIONS

Fan, C., et al., "Electrochemical interrogation of conformational changes as a reagentless method for the sequence-specific detection of DNA." Proc. Natl. Acad Sci., vol. 100, No. 16, pp. 9134-9137, 2003.

Ganesh, V., et al., "Self-assembled monolayers (SAMs) of alkoxycyanobiphenyl thiols on gold-A study of electron transfer reaction using cyclic voltammetry and electrochemical impedance spectroscopy." J Colloid Interface Sci., vol. 296, No. 1, pp. 195-203, Apr. 2006.

Grenier, C.J. et al., "Rapid, High Affinity Binding by a Fluorescein Templated Copolymer Combining Covalent, Hydrophobic, and Acid-Base Noncovalent Crosslinks", Sensors, 18(5): p. 1330-1-1330-11, (Year: Apr. 2018).

Haupt, Karsten, et al., "Molecularly Imprinted Polymers and Their Use in Biomimetic Sensors." Chemical Reviews, 2000, vol. 100, No. 7, pp. 2495-2504.

Jadhav, S.A., et al., "Synthesis of poly(N-isopropylacrylamide) by distillation precipitation polymerization and quantitative grafting on mesoporous silica." J. Appl. Polym. Sci., vol. 133, No. 44, 2016, p. 1-8.

Keefe, A., et al., "Aptamers as therapeutics." Nature Review / Drug Discovery, vol. 9, Jul. 2010, pp. 538-550.

Pilesky, S.A., et al., "Substitution of antibodies and receptors with molecularly imprinted polymers in enzyme-linked and fluorescent assays." Biosens. Bioelectron., vol. 16. No. 9-12, pp. 701-707, Dec. 2001.

Randviir, E. P. "A cross examination of electron transfer rate constants for carbon screen-printed electrodes using Electrochemical Impedance Spectroscopy and cyclic voltammetry." Electrochimica Acta, vol. 286, pp. 179-186, Oct. 2018.

Rogers, K. R., "Principles of affinity-based biosensors." Mal. Biotechnol., vol. 14, No. 2, pp. 109-129, Feb. 2000.

Sankar, M., et al., "Buffers for the Physiological pH Range: Thermodynamic Constants of 3-(NMorpholino) propanesulfonic Acid from 5 to 50 Â° C." Analytical Chemistry, vol. 50, No. 13, Nov. 1978, p. 1922-1924.

Selvaraju, T. et al., "Electrochemically deposited nanostructured platinum on Nafion coated electrode for sensor applications." J Electroanal. Chem., vol. 585, No. 2, pp. 290-300, 2005.

Steentjes, T., et al., "Electron Transfer Processes in Ferrocene-Modified Poly(ethylene glycol) Monolayers on Electrodes." Langmuir, vol. 33, No. 43, pp. 11878-11883, Oct. 2017.

Straka, M. M., et al., "Characterizing Longitudinal Changes in the Impedance Spectra of In-Vivo Peripheral Nerve Electrodes." Micromachines, vol. 9, No. 11, p. 587, Nov. 2018.

Tan, C., et al., "Detection of neurochemicals with enhanced sensitivity and selectivity via hybrid multiwall carbon nanotube-ultrananocrystalline diamond microelectrodes." Sens. Actuators B Chem., vol. 258, pp. 193-203, Apr. 2018.

Tarabukina, E., et al.,"Thermo-and pH responsive phase separation of N-isopropylacrylamide with 4-vinylpyridine random copolymer in aqueous solutions." Colloid Polym. Sci., vol. 296, No. 3, pp. 557-565, Mar. 2018.

Turner, Anthony P.F. "Biosensors: sense and sensibility," Chem. Soc. Rev., 2013, 42, 3184-3196.

Uzun, L., et al., "Molecularly imprinted polymer sensors: Realizing their potential." Biosens. Bioelectron., vol. 76, pp. 131-144, 2016.

White, R., et al., "Optimization of electrochemical aptamer-based sensors via optimization of probe packing density and surface chemistry." Langmuir, vol. 24, No. 18, pp. 10513-10518, 2008.

Yigit, M. V., "Smart 'turn-on' magnetic resonance contrast agents based on aptamer-functionalized superparamagnetic iron oxide nanoparticles." ChemBioChem, vol. 8, No. 14, pp. 1675-1678, Sep. 2007.

Zheng, Q., et al., "Preparation and characterization of dendrimer-star PNIPAAM using dithiobenzoate-terminated PPI dendrimer via RAFT polymerization." Eur. Polym. J, vol. 42, No. 4, pp. 807-814, Apr. 2006.

Zhou, J. et al., "RAFT-Mediate Polymerization-Induced Self-Assembly of Poly (Acrylic Acid)-b-Poly(Hexafluorobutyl Acrylate): Effect of the pH on the Synthesis of Self-Stablized Particles." Polymers, vol. 8, No. 6, 207, May 2016, p. 1-13.

SINGLE-CHAIN POLYMER-BASED TARGET RECEPTORS FOR USE IN ELECTROCHEMICAL DETECTION OF TARGET ANALYTES

CROSS-REFERENCE TO RELATED APPLICATIONS

This application is a continuation application of U.S. nonprovisional patent application Ser. No. 16/898,836, filed Jun. 11, 2020 and titled "SINGLE-CHAIN POLYMER-BASED TARGET RECEPTORS FOR USE IN ELECTROCHEMICAL DETECTION OF TARGET ANALYTES," which claims priority under 35 U.S.C. § 119 to U.S. provisional patent application No. 62/859,900, filed Jun. 11, 2019 and titled "SINGLE-CHAIN POLYMER-BASED TARGET RECEPTORS FOR USE IN ELECTROCHEMICAL DETECTION OF TARGET ANALYTES," the contents of which are incorporated herein by reference in their entirety.

BACKGROUND OF THE INVENTION

Using electrochemical methods for the identification and quantification of chemical species provides many advantages, such as low-cost implementation, fast readout, easy miniaturization and simple device architecture. In particular, voltammetric sensors utilize the target analyte's ability to be electrochemically oxidized or reduced and thereby generate an electron transfer between the analyte and the surface of the electrode—a chemical reaction can be transduced into an electrical current. Since voltammetric sensing relies on the analyte's redox activity, if other interfering chemicals with similar redox potentials are present in the sample solution, distinguishing the signal due to the analyte from that of the interfering species is difficult. Therefore, one of the key design parameters in developing an electrochemical sensor is optimizing chemical selectivity.

To enhance the target selectivity in electrochemical sensing, several strategies have been suggested and investigated. Some examples include coating an electrode surface with permselective polymer film (such as Nafion) to selectively attract species based on charges (T. Selvaraju and R. Ramaraj, "Electrochemically deposited nanostructured platinum on Nafion coated electrode for sensor applications," *J. Electroanal. Chem.*, vol. 585, no. 2, pp. 290-300, 2005), and immobilization of target capture units (such as antibodies and aptamers) on the surface of electrodes. Specifically, aptamer-based electrochemical sensing has seen much success in recent years due in part to its demonstration of continuous real-time monitoring of the analyte (N. Arroyo-Currás, J. Somerson, P. A. Vieira, K. L. Ploense, T. E. Kippin, and K. W. Plaxco, "Real-time measurement of small molecules directly in awake, ambulatory animals," *Proc. Natl. Acad. Sci. U.S.A*, vol. 114, no. 4, pp. 645-650, January 2017). Aptamer-based electrochemical sensing is based on the premise that when the target binds to the aptamer, it undergoes conformation change that can generate an electrochemically measurable signal through the use of a redox-active label attached to the terminus of the aptamer (C. Fan, K. W. Plaxco, and A. J. Heeger, "Electrochemical interrogation of conformational changes as a reagentless method for the sequence-specific detection of DNA," *Proc. Natl. Acad. Sci.*, vol. 100, no. 16, pp. 9134-9137, 2003; W. Plaxco, "Optimization of electrochemical aptamer-based sensors via optimization of probe packing density and surface chemistry," *Langmuir*, vol. 24, no. 18, pp. 10513-10518, 2008). The aptamer sequences are typically developed using an iterative and randomized screening process known as SELEX (A. D. Keefe, S. Pai, and A. Ellington, "Aptamers as therapeutics," *Nat. Rev. Drug Discov.*, vol. 9, no. 7, pp. 537-550, 2010). Indeed, many types of aptamers for a variety of target biomarkers and drugs have been developed. However, if a well-performing aptamer has not been identified for a particular analyte, the chemical selectivity in sensing may be compromised.

Another approach to enhance the chemical selectivity in electrochemical sensing has been through the molecular templating method, also known as molecular imprinting (L. Uzun and A. P. F. Turner, "Molecularlyimprinted polymer sensors: Realising their potential," *Biosens. Bioelectron.*, vol. 76, pp. 131-144, 2016; S. A. Piletsky, E. V Piletska, A. Bossi, K. Karim, P. Lowe, and A. P. Turner, "Substitution of antibodies and receptors with molecularly imprinted polymers in enzyme-linked and fluorescent assays," *Biosens. Bioelectron.*, vol. 16, no. 9-12, pp. 701-707, December 2001). Molecular templating is the technique where the polymer-based target receptor is synthesized in the presence of the templating molecule (e.g., the analyte) such that the polymer will capture the unique molecular features of the template, thereby "imprinting" the structure of the template into the polymer. This templated polymerization is done with the expectation that the polymer would exhibit preferential binding to the template molecule compared to other nonspecific molecules that may be regarded as interfering species.

Traditionally, molecularly imprinted polymers were based on a highly crosslinked polymer matrix with the imprinted molecular cavities buried in the bulk of the material. However, in this framework, the analyte must penetrate through the polymer matrix in order to find the binding sites, which leads to a slow rate of binding and release. Moreover, highly crosslinked polymers tend to be rigid, further hindering the accessibility of the imprinted molecular cavities for the target analyte.

SUMMARY OF THE INVENTION

The present disclosure provides embodiments of a new approach in developing templated polymer-based chemical receptors. Rather than a highly crosslinked polymer matrix, at least some embodiments of the invention relate to a single-chain template polymer that behaves as an analyte receptor. With this approach, it is expected that (1) the templated linear polymer binds and releases with the template molecule with reasonably high binding affinity and short response time, and (2) upon selective target binding, the polymer undergoes a conformation change from an extended conformation to a collapsed conformation.

At least some embodiments of the invention use a stimuli-responsive polymer [e.g., poly-Nisopropylacrylamide (pNIPAM)] as a polymer backbone with the incorporation of functional monomers (for analyte recognition). In at least some embodiments of the invention, vinylferrocene may be used as a redox-active label for the electrochemical transduction.

The polymer may enhance its binding affinity with the template molecule through intra-chain interactions, including hydrophobic crosslinks between N-isopropyl groups within the polymer chain as well as the acid-base crosslinks between anionic and cationic functional monomers, which, in some embodiments of the invention, may be incorporated during polymerization processing. In at least some embodiments of the invention, a redox-tagged templated polymer exhibits selective detection of the analyte 4-nitrophenol with sensitivity and selectivity.

An aspect of the present disclosure relates to an electrochemical sensor comprising a single-chain polymer attached to a surface, wherein the single-chain polymer is capable of selectively binding a target analyte, and wherein the selective binding detectably alters the conformation of the single-chain polymer. In at least some embodiments of the invention, the single-chain polymer further comprises one or more functional monomers. In at least some embodiments of the invention, the one or more functional monomers is one or more of a carboxylic acid and a pyridine derivative. In at least some embodiments of the invention, the carboxylic acid is methacrylic acid (MAA). In at least some embodiments of the invention, the pyridine derivative comprises a vinyl group. In at least some embodiments of the invention, the pyridine derivative comprises 4-vinylpyridine (4-VP). In at least some embodiments of the invention, the single-chain polymer further comprises a redox reporter. In at least some embodiments of the invention, the redox reporter comprises an organometallic compound. In at least some embodiments of the invention, the organometallic compound comprises a transition metal. In at least some embodiments of the invention, the transition metal comprises iron. In at least some embodiments of the invention, the organometallic compound comprises a vinyl group. In at least some embodiments of the invention, the organometallic compound comprises vinylferrocene. In at least some embodiments of the invention, the organometallic compound is a terminal monomer of the single-chain polymer. In at least some embodiments of the invention, the surface comprises a metal. In at least some embodiments of the invention, the metal comprises at least one of gold, carbon, platinum, silicon, silicon dioxide, and silver. In at least some embodiments of the invention, the target analyte comprises 4-nitrophenol (4-NP). In some embodiments of the invention, the target analyte comprises a toxin, optionally a neurotoxin, and optionally an excitotoxin. In at least some embodiments of the invention, the target analyte comprises glutamate. In at least some embodiments of the invention, the glutamate comprises L-glutamate. In at least some embodiments of the invention, the single-chain polymer comprises an N-isopropaylcrylamide (NIPAM) backbone.

Another aspect of the present disclosure relates to a single-chain polymer for use in electrochemical sensing, comprising: a carboxylic acid monomer; a monomer comprising a derivative of pyridine with a vinyl group; an organometallic compound; and an N-isopropaylcrylamide (NIPAM) backbone. In at least some embodiments of the invention, the carboxylic acid comprises methacrylic acid (MAA). In at least some embodiments of the invention, the derivative of pyridine with the vinyl group comprises 4-vinylpyridine (4-VP). In at least some embodiments of the invention, the organometallic compound comprises a transition metal. In at least some embodiments of the invention, the transition metal is iron. In at least some embodiments of the invention, the organometallic compound comprises a vinyl group. In at least some embodiments of the invention, the organometallic compound comprises vinylferrocene. In at least some embodiments of the invention, the organometallic compound is a terminal monomer of the single-chain polymer. In at least some embodiments of the invention, the single-chain polymer further comprises repeating sequences of the carboxylic acid monomer and the monomer comprising the derivative of pyridine with the vinyl group.

A further aspect of the present disclosure relates to a method of generating a single-chain polymer for use in electrochemical sensing. In at least some embodiments of the invention, the method comprises adding a backbone compound, a carboxylic acid, a derivative of pyridine with a vinyl group, and an organometallic compound to an organic solvent to produce a solution. In at least some embodiments of the invention, the method comprises, in the presence of a reversible addition-fragmentation chain transfer (RAFT) agent, a template molecule, and an initiator, performing RAFT polymerization with respect to the solution to produce a single-chain polymer solution comprising a single-chain polymer reacted with the template molecule. In at least some embodiments of the invention, the method comprises removing the template molecule from the single-chain polymer solution, and isolating the single-chain polymer from the single-chain polymer solution. In at least some embodiments of the invention, the method further comprises deoxygenating the solution to produce a de-oxygenated solution, and performing the RAFT polymerization with respect to the de-oxygenated solution. In at least some embodiments of the invention, the deoxygenating comprises performing a freeze-pump-thaw process on the solution. In at least some embodiments of the invention, the RAFT polymerization is performed in the presence of nitrogen. In at least some embodiments of the invention, the solution is heated while the RAFT polymerization is performed. In at least some embodiments of the invention, the solution is heated to a temperature of about 70° C. In at least some embodiments of the invention, removing the template molecule comprises dialyzing the single-chain polymer solution. In at least some embodiments of the invention, the dialyzing is performed using tetrahydrofuran (THF). In at least some embodiments of the invention, the THF comprises 50% THF. In at least some embodiments of the invention, the isolating comprises lyophilizing the single-chain polymer solution to obtain a powder comprising the single-chain polymer. In at least some embodiments of the invention, the backbone compound comprises N-isopropylacrylamide (NIPAM). In at least some embodiments of the invention, the carboxylic acid comprises methacrylic acid (MAA). In at least some embodiments of the invention, the derivative of pyridine with the vinyl group comprises 4-vinylpyridine (4-VP). In at least some embodiments of the invention, the organometallic compound comprises a transition metal. In at least some embodiments of the invention, the transition metal is iron. In at least some embodiments of the invention, the organometallic compound comprises a vinyl group. In at least some embodiments of the invention, the organometallic compound comprises vinylferrocene. In at least some embodiments of the invention, the organic solvent comprises an ether. In at least some embodiments of the invention, the ether comprises a cyclic ether. In at least some embodiments of the invention, the cyclic ether comprises dioxane. In at least some embodiments of the invention, the RAFT agent comprises 2-(Dodecyl-thiocarbonothioylthio)-2-methyl-propanioc acid (DDMAT). In at least some embodiments of the invention, the template molecule corresponds to a molecule to be bound by the single-chain polymer when the single-chain polymer is incorporated into an electrochemical sensor. In at least some embodiments of the invention, the template molecule comprises 4-nitrophenol (4-NP). In at least some embodiments of the invention, the initiator comprises azobisisobutyronitrile (AIBN). In at least some embodiments of the invention, the backbone compound, the carboxylic acid, the derivative of pyridine with the vinyl group, and the organometallic compound are present in a mmol ratio of about 7.4:1:1.4:0.2.

A further aspect of the present disclosure relates to a method of generating an electrochemical sensor. In at least some embodiments of the invention, the method comprises obtaining a single-chain polymer comprising a carboxylic acid monomer, a monomer comprising a derivative of pyridine with a vinyl group, an organometallic compound, a monomer comprising a reversible addition-fragmentation chain transfer (RAFT) agent, and a backbone compound. In at least some embodiments of the invention, the method comprises generating a modified single-chain polymer by changing the RAFT agent to a thiol, and covalently linking the thiol to a sensor surface. In at least some embodiments of the invention, the generating comprises producing a solution by dissolving the single-chain polymer in a liquid with a reducing agent. In at least some embodiments of the invention, the liquid comprises water. In at least some embodiments of the invention, the water comprises deionized water. In at least some embodiments of the invention, the reducing agent comprises tris (2-carboxyethyl) phosphine (TCEP). In at least some embodiments of the invention, the covalently linking comprises contacting the sensor surface with the solution. In at least some embodiments of the invention, the sensor surface comprises a metal. In at least some embodiments of the invention, the metal comprises at least one of gold, carbon, platinum, silicon, silicon dioxide, and silver. In at least some embodiments of the invention, the carboxylic acid comprises methacrylic acid (MAA). In at least some embodiments of the invention, the derivative of pyridine with the vinyl group comprises 4-vinylpyridine (4-VP). In at least some embodiments of the invention, the organometallic compound comprises a transition metal. In at least some embodiments of the invention, the transition metal is iron. In at least some embodiments of the invention, the organometallic compound comprises a vinyl group. In at least some embodiments of the invention, the organometallic compound comprises vinylferrocene. In at least some embodiments of the invention, the organometallic compound is a terminal monomer of the modified single-chain polymer. In at least some embodiments of the invention, the backbone compound comprises N-isopropylacrylamide (NIPAM). In at least some embodiments of the invention, the single-chain polymer comprises repeating sequences of the carboxylic acid monomer and the monomer comprising the derivative of pyridine with the vinyl group. In at least some embodiments of the invention, the RAFT agent comprises 2-(Dodecyl-thiocarbonothioylthio)-2-methyl-propanioc acid (DDMAT). In at least some embodiments of the invention, the RAFT agent is a terminal residue of the single-chain polymer.

A further aspect of the present disclosure relates to a method for electrochemical sensing. In at least some embodiments of the invention, the method comprises contacting a sample with an electrochemical sensor comprising a surface modified with a covalently attached single-chain polymer comprising an N-isopropaylcrylamide (NIPAM) backbone, wherein the single-chain polymer is capable of selectively binding a target analyte, and wherein the selective binding detectably alters the conformation of the single-chain polymer. In at least some embodiments of the invention, the method comprises monitoring attachment of the target analyte to the single-chain polymer. In at least some embodiments of the invention, a means of monitoring the attachment comprises at least one of electrochemical impedance spectroscopy, amperometric monitoring, voltametric monitoring, and potentiometric monitoring. In at least some embodiments of the invention, the method further comprises releasing the target analyte from the single-chain polymer. In at least some embodiments of the invention, the releasing is performed after the monitoring. In at least some embodiments of the invention, the releasing comprises rinsing the single-chain polymer, having the target analyte bound thereto, with a solvent capable of binding the target analyte. In at least some embodiments of the invention, the solvent comprises deionized water. In at least some embodiments of the invention, the method further comprises monitoring the attachment for at least 1 millisecond, at least 5 minutes, at least 10 minutes, at least 30 minutes, at least 45 minutes, or more. In at least some embodiments of the invention, the target analyte comprises glutamate. In at least some embodiments of the invention, the glutamate comprises L-glutamate.

BRIEF DESCRIPTION OF THE DRAWINGS

For a more complete understanding of the present disclosure, reference is now made to the following description taken in conjunction with the accompanying drawings.

DETAILED DESCRIPTION

Polymer Compositions

Figure 1:
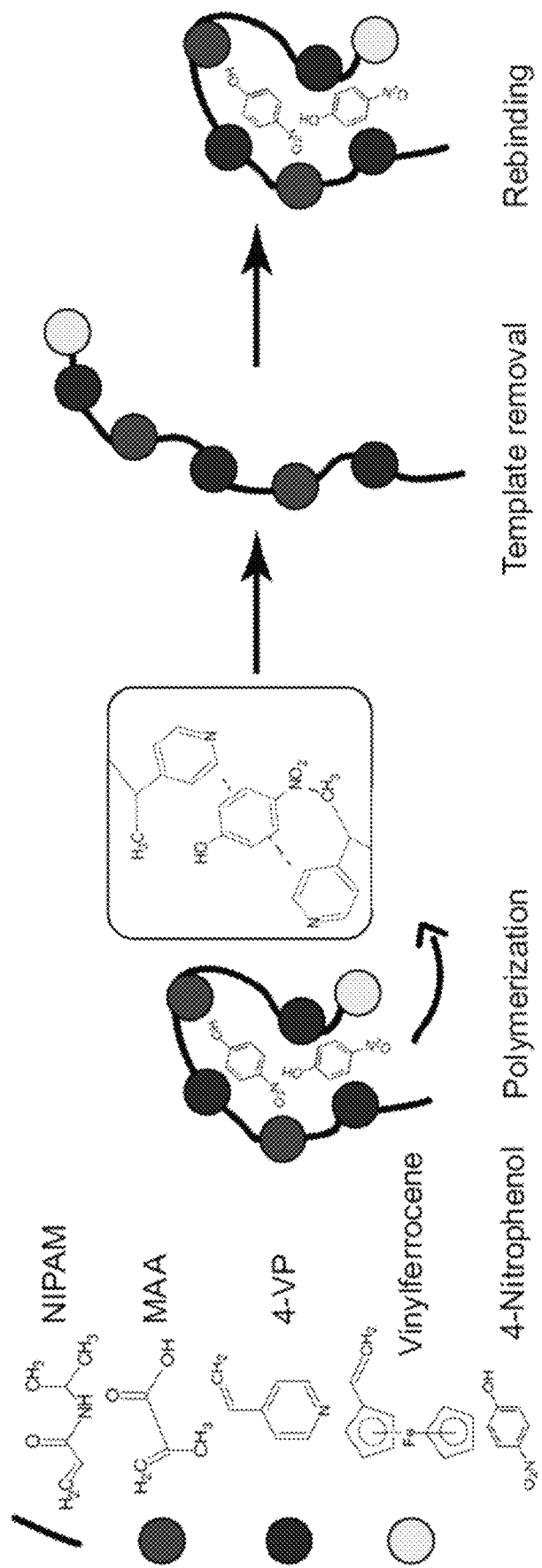
FIG. 1 is a conceptual diagram illustrating a concept of molecular recognition using a single-chain template polymer, in accordance with embodiments of the invention.

Certain aspects of the present disclosure relate to polymers that behave as analyte receptors. As used herein, a "polymer" is a macromolecule having repeating subunits (e.g., monomers) coupled to a backbone.

In at least some embodiments of the invention, a polymer may be a single-chain polymer. As used herein, a "single-chain polymer" refers to a polymer whose backbone is linear (e.g., not branched).

As used herein, a "backbone" refers to a series of covalently bonded molecules that together create a continuous chain of the polymer. A backbone, envisioned by the present disclosure, may comprise any molecules, and any repeating sequence of molecules, that enable one or more functional monomers to bind to one or more target analytes.

In at least some embodiments of the invention, a backbone may include N-isopropylacrylamide (NIPAM). In some examples, a backbone may be a continuous chain of only NIPAM.

As used herein, a "functional monomer" is a monomer that provides specific chemical function to the polymer. In at least some embodiments of the invention, a functional monomer may provide the polymer with functionality and/or specificity for binding one or more target analytes A polymer of the present disclosure may include one or more functional monomers. Moreover, when a polymer includes more than one functional monomer, the functional monomers may be the same or different, also referred to herein as "independently selected."

In at least some embodiments of the invention, a polymer may include one or more functional monomers having a carboxylic acid group. More specifically, at least some polymers may include one or more functional monomers comprising methacrylic acid (MAA).

In at least some embodiments of the invention, a polymer may include one or more functional monomers including pyridine derivatives. A pyridine derivative of a functional monomer may include a vinyl group. In at least some embodiments of the invention, a pyridine derivative of a functional monomer may include 4-vinylpyridine (4-VP).

In at least some embodiments of the invention, a polymer may include one or more repeating sequences of a functional monomer having a carboxylic acid group and a pyridine derivative functional monomer.

In at least some embodiments of the invention, a polymer may include a redox reporter. The redox reporter may be an inner monomer of a polymer, or may be a terminal monomer of a polymer. Positioning of the redox reporter along the backbone of a polymer may be selected based on, among other things, the functional monomers of the polymer and/or the target analyte(s). In at least some embodiments, the only criteria for selecting the positioning of the redox reporter is that the redox reporter is capable of causing differing chemical signals based on whether the target analyte(s) is bound to the polymer.

The redox reporter may include an organometallic compound. As used herein, an "organometallic compound" refers to a compound containing at least one metal-carbon bond. The organometallic compound may, in at least some embodiments, include at least one transition metal. Embodiments of the present disclosure include organometallic compounds including iron. However, one skilled in the art will appreciate that organometallic compounds may include other transitions metals. In at least some embodiments of the invention, the organometallic compound may include one or more vinyl groups. An example vinyl group is vinylferrocene.

As used herein, an "analyte" or "target analyte" refers to a molecule, compound, or other chemical or biological species that is capable of being bound by a polymer. The target analyte, in at least some embodiments, may be 4-nitrophenol (4-NP) or glutamate and, more specifically, L-glutamate.

Binding of a target analyte to a polymer may cause the polymer to alter its confirmation. For example, binding of a target analyte to a polymer may cause the polymer to change from an extended conformation to a collapsed conformation.

Methods of Producing Polymers

Certain aspects of the present disclosure relate to techniques for producing polymers that behave as analyte receptors. In at least some embodiments of the invention, one or more polymers may be produced by adding one or more backbone compound, one or more compounds including one or more carboxylic acids, one or more compounds including one or more derivatives of pyridine with one or more vinyl groups, and one or more organometallic compounds to an organic solvent to produce a solution.

The one or more polymers may be produced by adding one or more backbone compound, one or more compounds including one or more carboxylic acids, one or more compounds including one or more derivatives of pyridine with one or more vinyl groups, and one or more organometallic compounds may be present in different ratios. In at least some embodiments, the one or more polymers may be produced by adding one or more backbone compound, one or more compounds including one or more carboxylic acids, one or more compounds including one or more derivatives of pyridine with one or more vinyl groups, and one or more organometallic compounds may be present in a mmol ratio of about 7.4:1:1.4:0.2.

The organic solvent may include ether. In some examples, the ether may include a cyclic ether such as, but not limited to, a cyclic ether including dioxane.

The solution may undergo a polymerization reaction to produce a polymer solution, and more particularly a single-chain polymer solution in some examples. In at least some embodiments of the invention, reversible addition-fragmentation chain transfer (RAFT) polymerization may be performed with respect to the solution to produce a single-chain polymer solution wherein one or more single-chain polymers are reacted with one or more template molecules.

The RAFT polymerization may be performed in the presence of a RAFT agent, a template molecule, and an initiator. In at least some embodiments, RAFT polymerization may be performed in the presence of nitrogen.

Generally, a RAFT agent takes the form of a thiocarbonylthio compound. In at least some embodiments, the RAFT agent may be 2-(Dodecyl-thiocarbonothioylthio)-2-methyl-propanioc acid (DDMAT).

The template molecule may, in at least some embodiments, be the target analyte to be bound by the produced polymer. In another some other embodiments, the template molecule may not by the target molecule, but may nonetheless cause the produced polymer to have a configuration sufficient for binding the target analyte. In at least some embodiments, the template molecule may be 4-nitrophenol (4-NP)

The initiator may be referred to as a radical source. The initiator may be a thermochemical initiator, or the interaction of gamma radiation with some reagent. In at least some embodiments, the initiator may be decomposing radical initiation such as, for example, azobisisobutyronitrile (AIBN).

RAFT polymerization is a controlled radical polymerization technique. Specifically, RAFT polymerization makes use of a chain transfer agent to control molecular weight and polydispersity of a polymer during free-radical polymerization. Generally, RAFT polymeration involves initiation, propagation, RAFT pre-equilibrium; re-initiation, main RAFT equilibrium, and termination stages.

The initiation stage refers to when the reaction is started by the initiator. When a decomposing initiator is used, the initiator decomposes to form two fragments that react with a single monomer molecule to yield a propagating (i.e., growing) polymeric radical.

The propagation stage refers to when radical chains are propagated in their active (i.e., radical) form.

The RAFT pre-equilibrium stage refers to when a polymeric radical with n monomer units reacts with the RAFT agent to form a RAFT adduct radical. The RAFT adduct radical undergoes a fragmentation reaction in either direction to yield either the starting species or a radical and a polymeric RAFT agent. This is a reversible step in which the intermediate RAFT adduct radical is capable of losing either the R group or the polymeric species.

The re-initiation stage refers to when the leaving group radical reacts with another monomer species, thereby starting another active polymer chain.

The main RAFT equilibrium stage refers to when, by a process of rapid interchange, the present radicals are shared among all species that have not yet undergone termination. In at least some instances, the radicals are shared equally, thereby causing chains to have equal opportunities for growth.

The termination stage refers to when chains, in their active form, react via bi-radical termination to form chains that cannot react furthers. This is known as a dead polymer. In at least some instance, the RAFT adduct radical is sufficiently hindered such that is does not undergo termination reactions.

Generally, oxygen may be undesirable because it affects the polymeration processing. For example, oxygen may change a molecular structure and can negatively affect sensing performances. Thus, in at least some examples, the polymerization reaction may be performed on de-oxygenated solution.

In at least some embodiments, a freeze-pump-thaw process may be performed on the solution to produce a de-oxygenated solution. A standard freeze-pump-thaw process, as known in the art, may be used. Generally, a freeze-pump-thaw process involves applying a vacuum to remove oxygen from solution, then freezing the solution to prevent oxygen from dissolving back into the solution. This process may be repeated as necessary.

In at least some embodiments, the solution (or the de-oxygenated solution) may be heated while RAFT polymerization is performed. The solution (or de-oxygenated solution) may be heated to various temperatures. By way of illustration, and not limitation, the solution (or de-oxygenated solution) may be heated to about 70° C.

In at least some embodiments, after the polymerization reaction is completed, the template molecule may be removed from the polymer solution. In at least some embodiments of the invention, the template molecule may be removed by dialyzing the polymer solution. As known in the art, dialysis is a filtration process where a membrane with a certain pore size will pass small molecules through while blocking larger molecules (e.g., polymers). In at least some embodiments of invention, template molecules may be significantly smaller than the polymers generated through polymeration. As such, in at least some embodiments of the invention, dialysis will allow template molecules to pass through while polymers are filtered. Dialyzing of the polymer solution may be performed using tetrahydrofuran (THF), in at least some embodiments. In at least some embodiments, the THF may be 50% THF.

After the template molecule is removed from the polymer solution, the polymer may be isolated. Such isolation may, in at least some embodiments, include lyophilizing the polymer solution to obtain a powder including the polymer. Such lyophilizing may include freezing the polymer solution, lowering the pressure, and then removing ice by sublimation, or by another suitable art-known means.

Electrochemical Sensors

Certain aspects of the present disclosure relate to electrochemical sensors having sensing surfaces capable of monitoring stimuli-responsive behavior. Electrochemical sensing surfaces envisioned by the present disclosure include, but are not limited to, metal surfaces including gold, platinum, silicon, silicon dioxide, silver, allows thereof, combinations thereof, and chemical equivalents thereof. The present disclosure also includes non-metal surfaces, such as carbon and the like.

One or more polymers may be attached to an electrochemical sensing surface. In at least some examples, polymers may be configured as a 2-dimensional array on an electrochemical sensing surface. That is, all of the electrochemical sensor may be attached to the electrochemical sensor surface at first ends of the polymers. In certain embodiments, no polymers of the electrochemical sensor may be free floating in solution.

There are several benefits to implementing polymers as a 2-dimensional rather than implementing the polymers on a surface in 3-dimensions. For example, 3-dimensionally implemented polymers may coalescence to some degree. In contrast, with respect to 2-dimensionally implemented polymers, analyte binding is controlled by surface coverage.

Monitoring collapse of polymer on itself, in a 2-dimensional polymer array, is different than monitoring 3-dimensional solution-based coalescence.

Moreover, polymer collapse, in a 2-dimensional array of polymer, could be gradual as a function of the analyte. This is different than 3-dimensional solution-based coalescence. Solution-based coalescence is typically an on-off behavior, where an analyte will trigger the agglomeration of many polymer molecules in the solution. Because polymer, of a 2-dimensional polymer array, is unlikely to interact with neighboring polymer, each polymer interacts with the analyte independently. Therefore, a 2-dimensional array of polymer may create a more gradual and measurable collapse behavior that could be calibrated to the quantity of analyte exposed to the 2-dimensional array of polymer.

In at least some embodiments, a 2-dimensional array of polymer, capable of binding target analyte, may be configured as part of an electrochemical sensor, and more particularly, in some examples, as part of an electrode of an electrochemical sensor. Illustrative electrodes that may include a 2-dimensional array of polymer may include, but are not limited to, gold electrodes, carbon electrodes, platinum electrodes, silicon electrodes, silicon dioxide electrodes, silver electrodes, and the like.

Methods of Producing Electrochemical Sensors

Certain aspects of the present disclosure relate to techniques for producing electrochemical sensors. Such techniques may include obtaining a polymer as described herein. In at least some embodiments, the polymer may include a monomer including a RAFT agent. In at least some embodiments, the RAFT agent may be a terminal residue of the polymer.

A modified polymer may be generated from the polymer. In embodiments where the polymer includes a monomer including a RAFT agent, the modified polymer may be generated by changing the RAFT agent to a thiol.

Generating the modified polymer may include producing a solution by dissolving the polymer in a liquid with at least one reducing agent. In at least some embodiments, the liquid may include water, and more particularly may include deionized water. The reducing agent may include tris (2-carboxyethyl) phosphine (TCEP), in at least some embodiments.

In embodiments wherein the modified polymer) is generated by changing the RAFT agent to a thiol, the thiol may be covalently linked to a sensor surface, thereby producing an electrochemical sensor in accordance with embodiments of the present disclosure. In at least some embodiments, covalent linking of the thiol to the sensor surface may include contacting the sensor surface with solution comprising the polymer dissolved in a liquid with at least one reducing agent.

Methods of Performing Electrochemical Sensing

Certain aspects of the present disclosure relate to techniques for performing electrochemical sensing. Electrochemical sensing, in accordance with embodiments of the present disclosure, may include contacting a sample with an electrochemical sensor having a surface modified with a covalently attached polymer. The polymer may selectively bind a target analyte. In at least some embodiments, the selective binding detectably alters a conformation of the polymer.

As detailed herein, a polymer may include a redox reporter. When the polymer is not bound to a target analyte, the polymer may exhibit a first conformation. In at least some embodiments, the polymer may be in an extended conformation when the polymer is not bound to a target analyte. When the polymer is not bound to a target analyte, the redox reporter may be a first distance away from the sensing surface to which the polymer is covalently attached. When the redox reporter is at the first distance, the electrochemical sensor may measure a first signal relating to the redox reporter's distance to the sensing surface.

When the polymer binds a target analyte, the polymer may exhibit a second conformation. In at least some embodiments, the polymer may be in a collapsed conformation when the polymer is bound to a target analyte. When the polymer is bound to a target analyte, the redox reporter may be a second distance away from the sensing surface to which the polymer is covalently attached. This second distance may be different form the first distance. In at least some embodiments, the second distance may be less than the first distance (e.g., the redox reporter is closer to the sensing surface when the polymer is in a collapsed conformation as compared to when the polymer is in the extended conformation). When the redox reporter is at the second distance, the electrochemical sensor may measure a second signal relating to the redox reporter's distance to the sensing surface. The second signal may be different from the first signal. The measured signal changing from the first signal to the second signal may indicate the polymer has bound a target analyte.

In at least some embodiments, monitoring attachment of a target analyte to polymer may include at least one of electrochemical impedance spectroscopy, amperometric monitoring, voltametric monitoring, and potentiometric monitoring. Monitoring attachment of analyte to polymer may occur over various amounts of time. For example, monitoring attachment may occur for at least 1 millisecond, at least 5 minutes, at least 10 minutes, at least 30 minutes, at least 45 minutes, or more.

In at least some embodiments, binding of a target analyte to polymer may be reversible. That is, the polymer may be caused to release the target analyte. In at least some embodiments, target analyte may become unbound from polymer by rinsing (e.g., continuously) with deionized water or some other solvent capable of binding the target analyte. In at least some other embodiments, the polymer with analyte bound thereto may be removed from the sensor surface. Thereafter, polymer, without analyte attached thereto, may be covalently attached to the surface. The resulting surface could then be used to perform monitoring as discussed above. The foregoing techniques may be beneficial because they permit the electrochemical sensor to be reusable.

Methods of Measuring Binding Affinity Template Polymers

Figure 11:
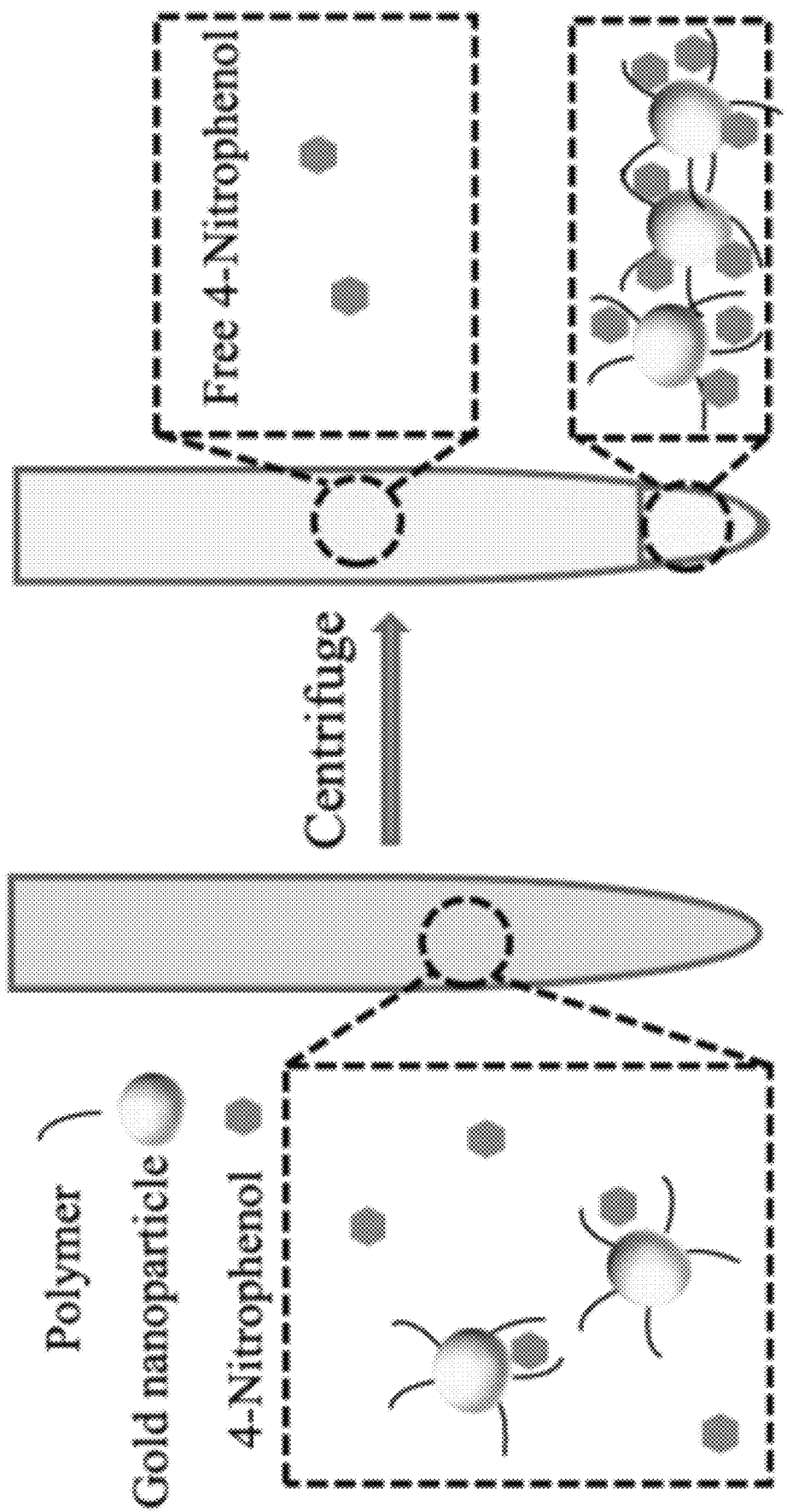
FIG. 11 shows the process of determining the binding affinity of the template polymers using gold nanoparticles (AuNPs) and UV-vis. The level of rebinding was determined following centrifugation.

Binding affinity of template polymers may be measured in a variety of manners. In at least some embodiments of the invention, as illustrated in FIG. 11, a target polymer, gold nanoparticles, and a target analyte may be placed in a test tube (or other container) in an appropriate solvent(s). UV-vis spectroscopy may then be performed on the solution to obtain a reference absorbance.

The solution may then be centrifuged to cause bound target polymer/target analytes to fall out of solution. UV-vis spectroscopy may then be performed on the centrifuged sample to obtain a second absorbance.

A measure of binding affinity may be determined based on a difference between the reference absorbance and the post-centrifugation absorbance.

EXAMPLES

Example 1

Polymer Synthesis

Polymers were prepared via RAFT polymerization. In brief, 7.4 mmol of NIPAM, 1 mmol of MAA, 1.4 mmol of 4-VP, and 0.2 mmol of vinylferrocene were added in 100 mL dioxane solution for molecular assembly. The RAFT chain transfer agent used was 0.1 mmol of DDMAT. The amount of template molecules, 4-NP, added for the polymerization was 0.1 mmol. The initiator was 0.05 mmol of AIBN. A freeze-pump-thaw process was carried out to extract the dissolved oxygen in the mixed solution, followed by filling the flask with nitrogen to balance the pressure. Then the flask was heated to 70° C. during polymerization. Once the polymerization was complete, the polymer solution was dialyzed against 50% THF to remove the templates and the unreacted species. Finally, the remaining polymer solution in the dialysis bag was dried out in a lyophilizer to obtain the polymer powder.

FIG. 1 depicts a concept of molecular recognition using a single-chain templated polymer. The molecular orientation of the template 4-NP is 'imprinted' by the polymer chain during polymerization. When the template is removed from the polymer, the chain stretches out to a random coil. However, when the template rebinds to the receptor, the polymer conformation is returned to a collapsed conformation.

Sensor Electrode Preparation

The RAFT chain transfer agent attached at the end of the polymer was used to anchor the polymers to the electrode surface. Briefly, obtained polymer powder and TCEP were dissolved in deionized water, and a gold electrode was immersed in the mixture. TCEP is a reducing agent frequently used in ligand binding chemistry (M. V. Yigit, D. Mazumdar, H. K. Kim, J. H. Lee, B. Odintsov, and Y. Lu, "Smart 'turn-on' magnetic resonance contrast agents based on aptamerfunctionalized superparamagnetic iron oxide nanoparticles," ChemBioChem, vol. 8, no. 14, pp. 1675-1678, September 2007). In the presence of TCEP, the RAFT agent residue at the end of the polymer chain converts to a thiol, which can then be used to form a covalent link to the gold surface.

Electrochemical Characterization and Sensing Protocol

Electrochemical characterization and sensing were arried out in a MOPS ((3-(N-morpholino) propane sulfonic acid) buffer solution. The MOPS buffer contained sodium hydroxide (NaOH) in order to adjust the pH level to 7.0. Cyclic voltammetry (CV) was performed at a scan rate of 100 mV/s from −0.2 V to +1.5 V vs. an Ag/AgCl reference. Differential pulse voltammetry (DPV) was performed with an amplitude of 250 mV with step voltage of 5 mV from −0.2 V to +0.7 V vs. Ag/AgCl in 1M $NaClO_4$ in deionized water with pH 7.0. Electrochemical experiments were carried out in a glass cell and a platinum wire was used as a counter electrode. All electrochemical experiments were performed using Bio-Logic VSP dual channel potentiostat.

Figure 2A:
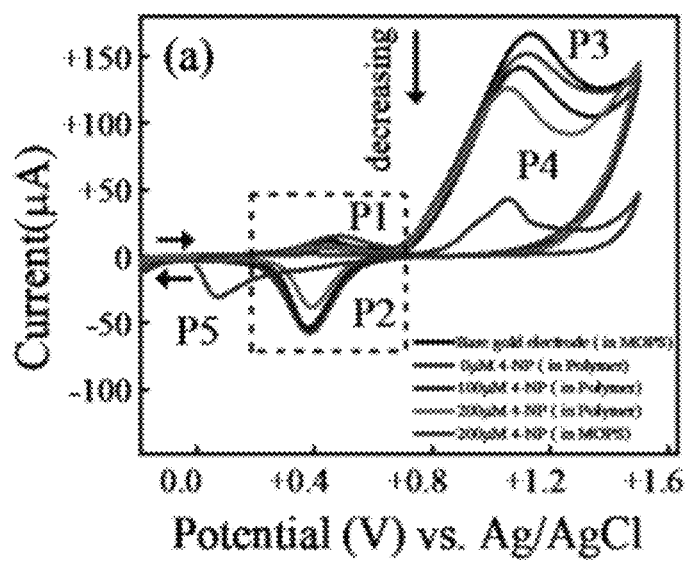
FIG. 2(a) is a cyclic voltammetry (CV) plot of a 4-nitrophenol (4-NP) sensor during each stage of electrode modification, in accordance with embodiments of the present disclosure. The horizontal arrows indicate the direction of the forward and reverse sweep of CV.
Figure 2B:
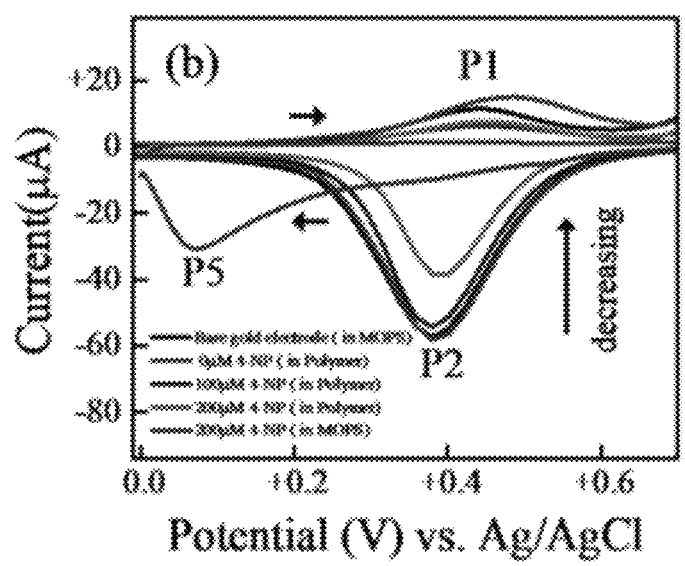
FIG. 2(b) is a magnified view of peaks P1 and P2 of FIG. 2(a), in accordance with embodiments of the present disclosure. A gradual decrease in MOPS ((3-(N-morpholino) propane sulfonic acid) oxidation and reduction upon polymer deposition and 4-NP binding is observed.

Electrochemical Characterization of Templated Polymer without Vinylferrocene Redox Tag Initial electrochemical analysis was performed through CV of the electrode during various stages of the electrode modification from bare electrode to polymer attachment and exposure to 4-NP. After the templated polymer attachment, the electrode was exposed to 4-NP to allow them to bind to the polymer receptors, followed by rinsing the electrode to remove any unbound 4-NP molecules. FIG. 2 shows CV curves in MOPS buffer for a bare electrode (black), polymer attached electrode (red), and after 4-NP analyte was bound to the polymers (blue and green). FIG. 2 also shows the CV curve for the bare electrode with 4-NP added to the MOPS buffer (purple).

During the CV cycles, some radical species present in the MOPS buffer acted as interferants during voltammetry (M. Sankar et al., "Buffers for the Physiological pH Range: Thermodynamic Constants of 3-(NMorpholino) propane-sulfonic Acid from 5 to 50° C.," J. Chem. Eng. Data, vol. 42, no. 13, pp. 41-44, March 1997; L. Ai and J. Jiang, "Catalytic reduction of 4-nitrophenol by silver nanoparticles stabilized on environmentally benign macroscopic biopolymer hydrogel," Bioresour. Technol., vol. 132, pp. 347-377, March 2013). In FIG. 2, the peaks P1 and P2 are attributed to the anionic (B) and cationic (A) radicals generated from the MOPS buffer during CV as shown in the redox reaction below:

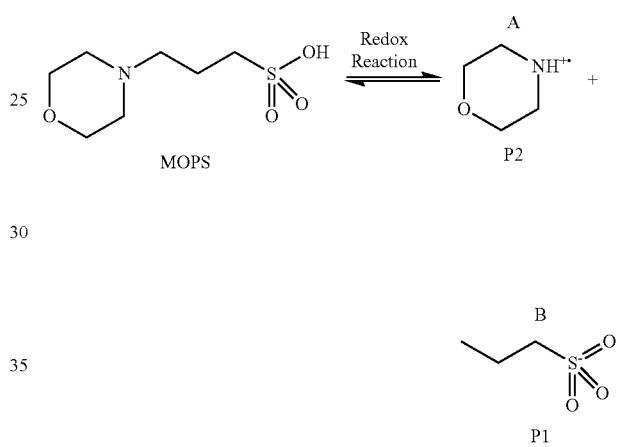

Also, the broad anodic peak P3 in the forward sweep (which has no cathodic counterpart on the subsequent backward sweep) can be attributed to the formation of monolayer oxide ($Au_2O_3$) growth at the electrode surface (L. D. Burke and P. F. Nugent, "The electrochemistry of gold: I. The redox behaviour of the metal in aqueous media," Gold Bull., vol. 30, no. 2, pp. 43-53, June 1997) due to the presence of NaOH species in MOPS.

Upon polymer attachment and 4-NP binding, a gradual decrease in the peaks P1, P2, and P3 are observed. This peak decrease signifies a gradual reduction in the electroactive area of the gold surface due to the polymer attachment and collapse upon target binding. The presence of the polymers on the electrode surface restricts the diffusion of MOPS buffer radicals as well as the 4-NP binding. It is worth noting that the peaks P1, P2, and P3 are not due to the adsorption-based oxidation of 4-NP at the electrode. Instead, the peaks P4 and P5 correspond to the redox activity due to the bulk diffusion of 4-NP. The fact that only peaks P4 and P5 appear for the 4-NP present in MOPS (purple) indicates that the rate of reaction for 4-NP is much higher than MOP oxidation. The peak oxidation current for 4-NP (P4) is 31.4 μA, which is 4 to 10 times higher than the MOPS peak oxidation current (P1). The peak potential due to gold surface oxidation (P3) is higher than +1.0 V compared to 4-NP oxidation peak (P4) as summarized in Table 1.

TABLE 1

The peak currents and the corresponding potentials of CV upon the polymer deposition and 4-NP binding in MOPS buffer at pH 7. The table also shows the oxidation and reduction characteristics of 4-NP at bare gold electrode.

| Table 2 | MOPS oxidation Peak P1 | | MOPS reduction Peak P2 | | Base Oxidation Peak P3 | |
|---|---|---|---|---|---|---|
| Samples | $E_1$ (V) | $I_1$ (μA) | $E_2$ (V) | $I_2$ (μA) | $E_3$ (V) | $I_3$ (μA) |
| Bare Gold | 0.43 | 7.8 | 0.37 | −54.8 | 1.13 | 89.1 |
| Polymer deposited Gold | 0.48 | 9.2 | 0.38 | −56.1 | 1.11 | 87.3 |
| 100 μM 4-NP (Polymer) | 0.44 | 5.9 | 0.37 | −52.9 | 1.09 | 80.2 |
| 200 μM 4-NP (Polymer) | 0.44 | 4.2 | 0.39 | −37.2 | 1.05 | 71.6 |

| | 4-NP oxidation Peak P4 | | 4-NP reduction Peak P5 | |
|---|---|---|---|---|
| | Potential | Current | Potential | Current |
| Bare Gold | 1.03 V | 31.4 μA | 0.07 V | −22.7 μA |

The occurrence of the highly anodic peak (P3) at the polymer functionalized and 4-NP bound surface causes the generation of radical OH· or oxygen species that may initiate further oxidation of the bare electrode surface to gold oxide, further hindering the diffusion-based charge transfer for detecting 4-NP. Therefore, another detection strategy may be beneficial, which does not oxidize the gold surface and yet provide the change in signal due to the conformational change in the polymer upon 4-NP binding. This can be achieved by introducing redox tags, such as vinylferrocene, into the polymer backbone.

Vinylferrocene-Tagged Templated Polymer Characterization

Figure 3A:
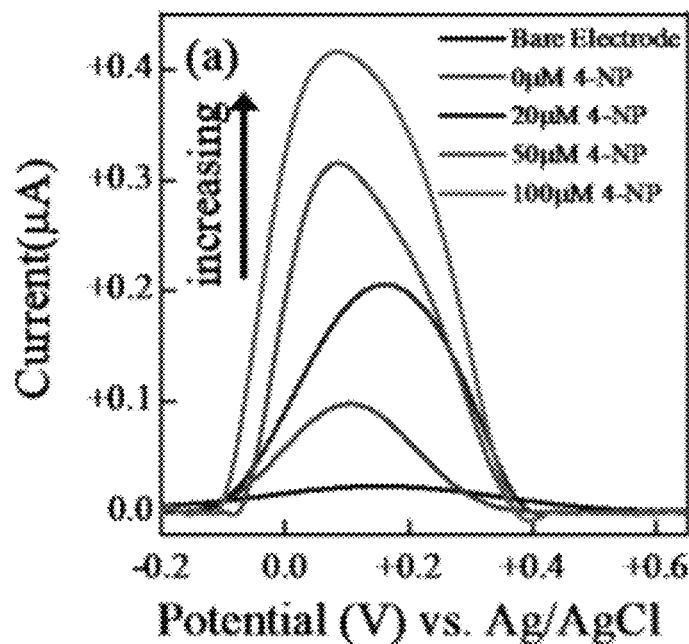
FIG. 3(a) is a differential pulse voltammetry (DPV) plot after binding of different concentrations of 4-NP, immobilized after deposition of functionalized polymer on a gold electrode, in accordance with embodiments of the present disclosure. The electrolyte is 1M $NaClO_4$ with pH. 7.
Figure 3B:
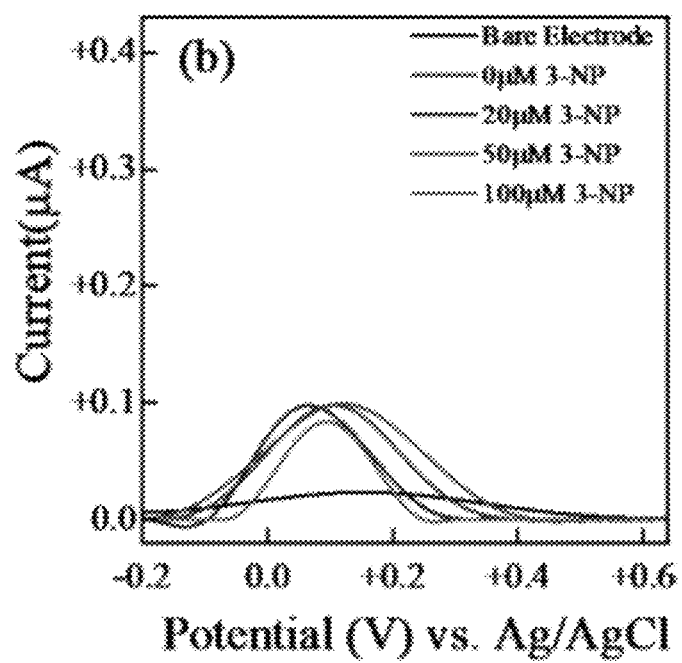
FIG. 3(b) is a DPV plot after binding of varying levels of 3-nitrophenol (3-NP), immobilized after deposition of functionalized polymer on a gold electrode, in accordance with embodiments of the present disclosure. The electrolyte is 1M $NaClO_4$ with pH. 7.

To enhance the redox signal from the vinylferrocene attached to the polymer, 1M $NaClO_4$ was used as a buffer (T. Steentjes, P. Jonkheijm, and J. Huskens, "Electron Transfer Processes in Ferrocene-Modified Poly(ethylene glycol) Monolayers on Electrodes," *Langmuir*, vol. 33, no. 43, pp. 11878-11883, October 2017). DPV was adopted to reduce the background noise and amplify the ferrocene signal for 4-NP detection. FIG. 3(a) shows that upon binding of different concentrations of 4-NP, there is a gradual increase in signal, which confirms the polymers collapse as they bind with 4-NP. When the polymers are in the extended conformation, the ferrocene tags are positioned away from the gold surface, inhibiting the redox transfer and therefore resulting in smaller DPV signal. Upon binding of 4-NP, the ferrocene tags move nearer the gold surface due to the polymer collapsing, resulting in enhanced charge transfer. The amplified signal confirms that the polymer transforms from a coil (extended conformation) to a globular form (collapsed conformation) (T. Steentjes, P. Jonkheijm, and J. Huskens, "Electron Transfer Processes in Ferrocene-Modified Poly (ethylene glycol) Monolayers on Electrodes," *Langmuir*, vol. 33, no. 43, pp. 11878-11883, October 2017). Furthermore, FIG. 3(b) demonstrates chemical selectivity against an isomer, 3-nitrophenol (3-NP), where minimal change in the DPV signal was observed.

Sensing Performances and Calibration Curve

Figure 4A:
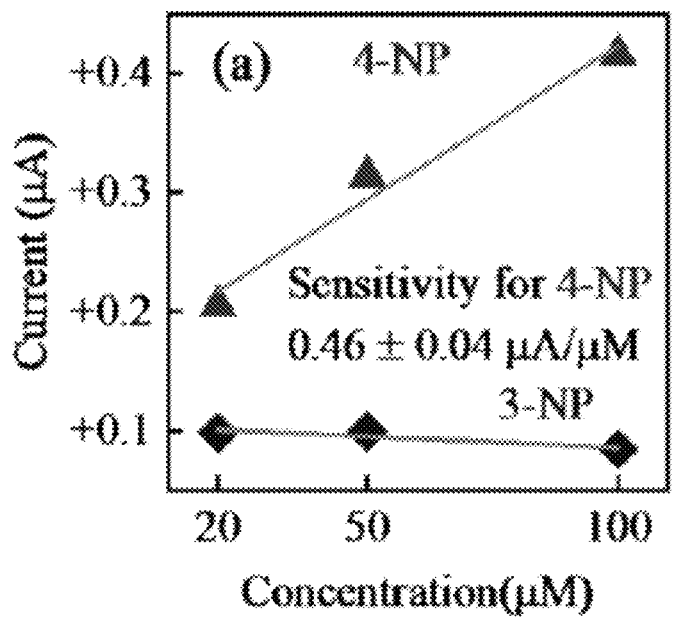
FIG. 4(a) shows calibration curves (peak current vs. concentration) for target analyte (4-NP) and non-specific interfering species (3-NP), in accordance with embodiments of the present disclosure.
Figure 4B:
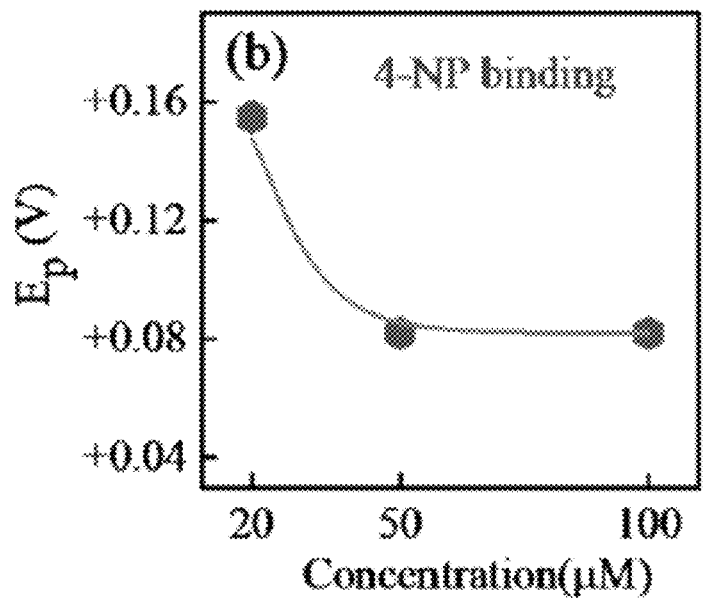
FIG. 4(b) shows a shift in the peak potential vs. concentration indicating a change in polymer conformation as a result of 4-NP binding, in accordance with embodiments of the present disclosure.

The redox tagged sensor signal in FIG. 4(a) shows an almost linear response upon analyte binding to polymer-based receptors. The sensitivity slope calculation for 3-NP is almost zero, which shows significant selectivity against 3-NP. The sensitivity for 4-NP detection was calculated to be 460 nA/uM. Also, the peak potential (Ep) vs. concentration plot in FIG. 4(b) shows a cathodic shift in Ep upon 4-NP binding, which demonstrates enhanced charge transfer kinetics due to polymer conformation change. As the 4-NP concentration increases, the potential EP decreases to about +0.08 V, indicating that more ferrocene tags are in close proximity to the electrode surface, suggesting a greater polymer collapse into a globular formation (collapsed conformation).

Conclusion

A single-chain pNIPAM-based templated polymer was developed that can selectively measure 4-NP. Such functionalized polymer tagged with ferrocene was able to show improved sensitivity and selectivity. Furthermore, upon target binding, the polymer underwent conformation change from a random coil to a globular form which, in turn, enhanced the electrochemical signal for the redox tagged functional polymers. The herein disclosed sensing strategy further reduces background noise, and signals from other interfering species and oxygen evolution, rendering it an effective platform for the selective detection of analytes.

Example 2

Polymer Synthesis

Figure 5A:
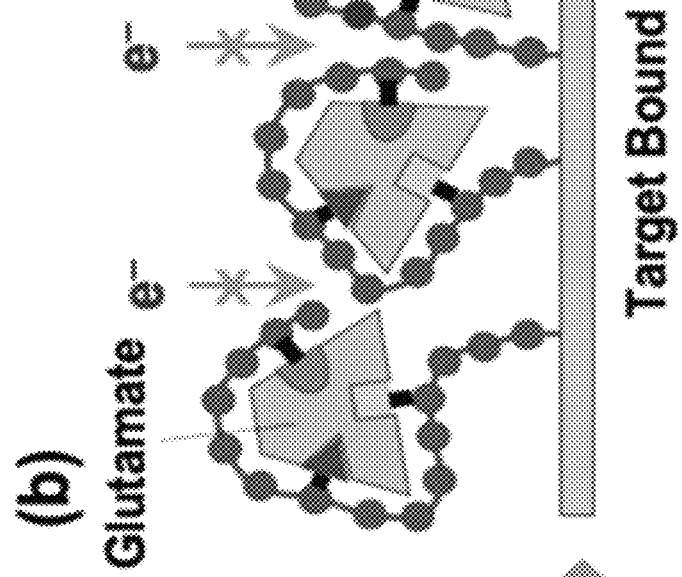
FIG. 5(a) is a schematic representation of a sensor surface with polymers unbound to glutamate, in accordance with embodiments of the present disclosure.
Figure 5B:
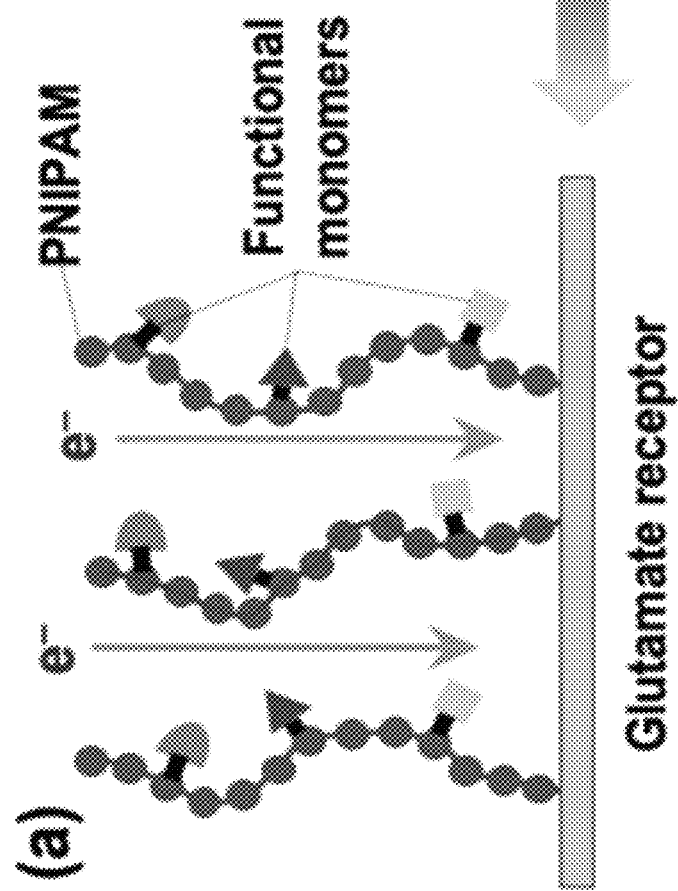
FIG. 5(b) is a schematic representation of a sensor surface with polymers bound to glutamate, in accordance with embodiments of the present disclosure.

Polymer, capable of binding the target analyte glutamate (Glu), was developed using a single-chain PNIPAM copolymerized with functional monomers 4-VP and MAA (C. J. Grenier et al., "Rapid, High Affinity Binding by a Fluorescein Templated Copolymer Combining Covalent, Hydrophobic, and Acid-Base Noncovalent Crosslinks," *Sensors*, vol. 18, no. 5, April 2018). The synthesized polymer exhibited a lower critical solution temperature (LCST) of 31-33° C. (C. Boyer and T. P. Davis, "One-pot synthesis and biofunctionalization of glycopolymers via RAFT polymerization and thiol-ene reactions," *Chem. Commun.*, vol. 0, no. 40, pp. 6029-6031, October 2009). FIGS. 5(a) and 5(b) conceptually show the a polymer before and after binding of Glu. The polymers were synthesized via the RAFT method in the presence of N-methylglutamic acid (Methyl-Glu) as a template. The methylated glutamate analog was used instead of Glu to prevent cross-reaction between the primary amine group of the Glu and the RAFT agent (C. Boyer and T. P. Davis, "One-pot synthesis and biofunctionalization of glycopolymers via RAFT polymerization and thiol-ene reactions," *Chem. Commun.*, vol. 0, no. 40, pp. 6029-6031, October 2009), resulting in significantly higher polymerization yield.

The synthesis of Methyl-Glu templated polymers were performed by mixing 8.7 mmol of NIPAM, 0.5 mmol of MAA, 0.8 mmol of 4-VP, 0.1 mmol of RAFT chain transfer agent (CTA) 2-(Dodecylthio-carbonothioylthio)-2-methyl-propanoic acid (DDMAT), 0.1 mmol of template molecule Methyl-Glu, and 0.01 mmol of AIBN in 35 mL dioxane solution. The freeze-pump-thaw process was performed three times for degassing. Finally, the polymerization was initiated at 70° C. After the polymerization was complete, the product was dialyzed against 50% THF to remove the template and the unreacted species. The polymer powder was then obtained via lyophilization after purification.

For sensor development, the polymers were attached to a gold electrode in the presence of the reducing agent TCEP to promote thiol bonding (M. V. Yigit, D. Mazumdar, H.-K. Kim, J. H. Lee, B. Odintsov, and Y. Lu, "Smart 'Turn-on' Magnetic Resonance Contrast Agents Based on Aptamer-Functionalized Superparamagnetic Iron Oxide Nanoparticles," *ChemBioChem*, vol. 8, no. 14, pp. 1675-1678, 2007). Glu rebinding to the polymer was performed via immersing the polymerized electrode in a Glu solution (at pH 7.0) prepared in deionized water for 5 minutes. Afterward, the sensor was washed in deionized water in order to minimize nonspecific bindings of Glu to the polymers.

NMR Analysis of Polymer

Figure 6:
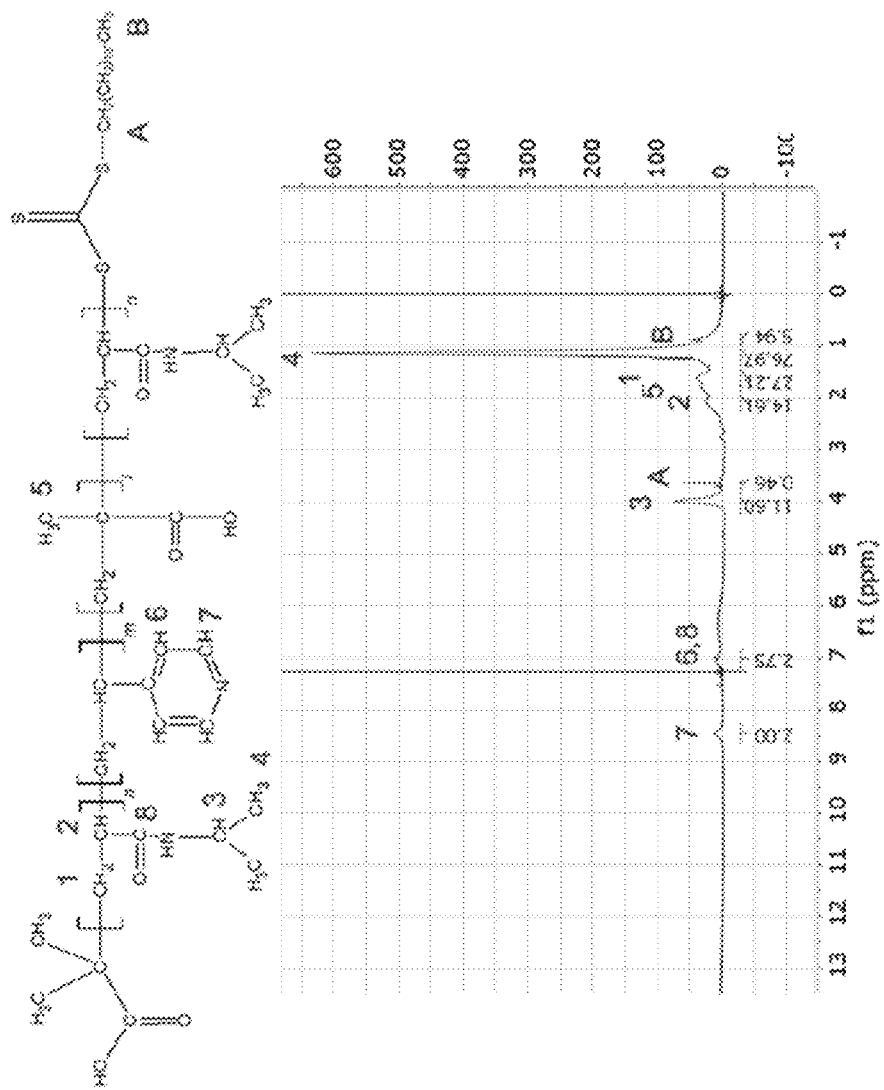
FIG. 6 shows the chemical structure of Methyl-Glu templated polymer after template removal and the corresponding 1H-NMR spectrum, in accordance with embodiments of the present disclosure.

The composition and structure of the Methyl-Glu templated polymer were determined by 1H-NMR spectroscopy. FIG. 6 shows the theoretical structure of the polymer and the corresponding NMR spectrum (S. A. Jadhav, V. Brunella, I. Miletto, G. Berlier, and D. Scalarone, "Synthesis of poly (N-isopropylacrylamide) by distillation precipitation polymerization and quantitative grafting on mesoporous silica," *J. Appl. Polym. Sci.*, vol. 133, no. 44, 2016; J. Zhou, R. He, and J. Ma, "RAFT-Mediated Polymerization-Induced Self-Assembly of Poly(Acrylic Acid)-b-Poly(Hexafluorobutyl Acrylate): Effect of the pH on the Synthesis of Self-Stabilized Particles," *Polymers*, vol. 8, no. 6, p. 207, June 2016; Q. Zheng and C. Pan, "Preparation and characterization of dendrimer-star PNIPAAM using dithiobenzoateterminated PPI dendrimer via RAFT polymerization," *Eur. Polym. J.*, vol. 42, no. 4, pp. 807-814, April 2006; and E. Tarabukina, A. Rozanova, A. Filippov, M. Constantin, V. Harabagiu, and G. Fundueanu, "Thermo- and pHresponsive phase separation of N-isopropylacrylamide with 4-vinylpyridine random copolymer in aqueous solutions," *Colloid Polym. Sci.*, vol. 296, no. 3, pp. 557-565, March 2018). The δ=4.0 ppm and δ=1.1 ppm are attributed to methine protons and methyl protons of NIPAM, respectively (E. Tarabukina, A. Rozanova, A. Filippov, M. Constantin, V. Harabagiu, and G. Fundueanu, "Thermo- and pHresponsive phase separation of N-isopropylacrylamide with 4-vinylpyridine random copolymer in aqueous solutions," *Colloid Polym. Sci.*, vol. 296, no. 3, pp. 557-565, March 2018). δ=8.5 and δ=7.1 ppm are attributed to aromatic protons of 4-VP (Q. Zheng and C. Pan, "Preparation and characterization of dendrimer-star PNIPAAM using dithiobenzoateterminated PPI dendrimer via RAFT polymerization," *Eur. Polym. J.*, vol. 42, no. 4, pp. 807-814, April 2006). The feature signals of DDMAT were observed at δ=3.64 ppm (—SCH$_2$(CH$_2$)$_{10}$CH$_3$) and at δ=0.9 ppm (—S—CH$_2$(CH$_2$)$_{10}$CH$_3$) (Q. Zheng and C. Pan, "Preparation and characterization of dendrimer-star PNIPAAM using dithiobenzoateterminated PPI dendrimer via RAFT polymerization," Eur. Polym. vol. 42, no. 4, pp. 807-814, April 2006). The molar ratio between functional monomer 4-VP and NIPAM can be calculated via equation (1) below:

$$\frac{\text{Mol}(4-VP)}{\text{Mol}(NIPAM)} = \left[\frac{A_1/2_{(protons)}}{A_2/1_{(proton)}}\right] \quad \text{Equation (1)}$$

where $A_1$ is the area of aromatic protons at 8.5 ppm, and $A_2$ is the area of methine protons of isopropyl group at 4.0 ppm. The calculated ratio is 8:92.8, which is in close agreement with the initial composition (8:87) during synthesis.

Experimental Setup

Electrochemical characterization and sensing were carried out in a 5 mM potassium ferro/ferricyanide $K_{4/3}$Fe(CN)$_6$ dissolved in 1×PBS buffer. The pH level recorded was 7.2. CV was performed at a scan rate of 100 mV/s from 0 V to +0.8 V vs. Ag/AgCl reference. Electrochemical impedance spectroscopy (EIS) was performed with an amplitude of 10 mV with frequencies ranging from 1 Hz to 100 KHz. All circuit fitting was performed using EC-lab software to obtain the circuit parameters. Electrochemical experiments were carried out in a glass cell, and a platinum wire used as a counter electrode. A Bio-Logic VSP dual channel potentiostat was used for all electrochemical studies.

Results and Discussion

Figure 7A:
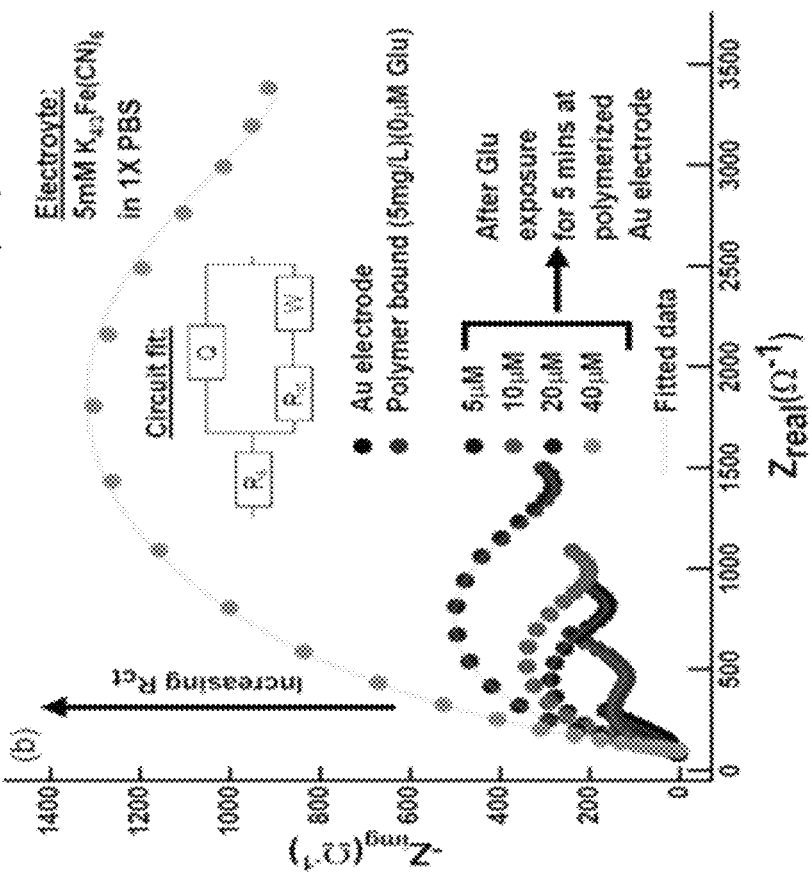
FIG. 7(a) shows a change in CV curves, in accordance with embodiments of the present disclosure.
Figure 7B:
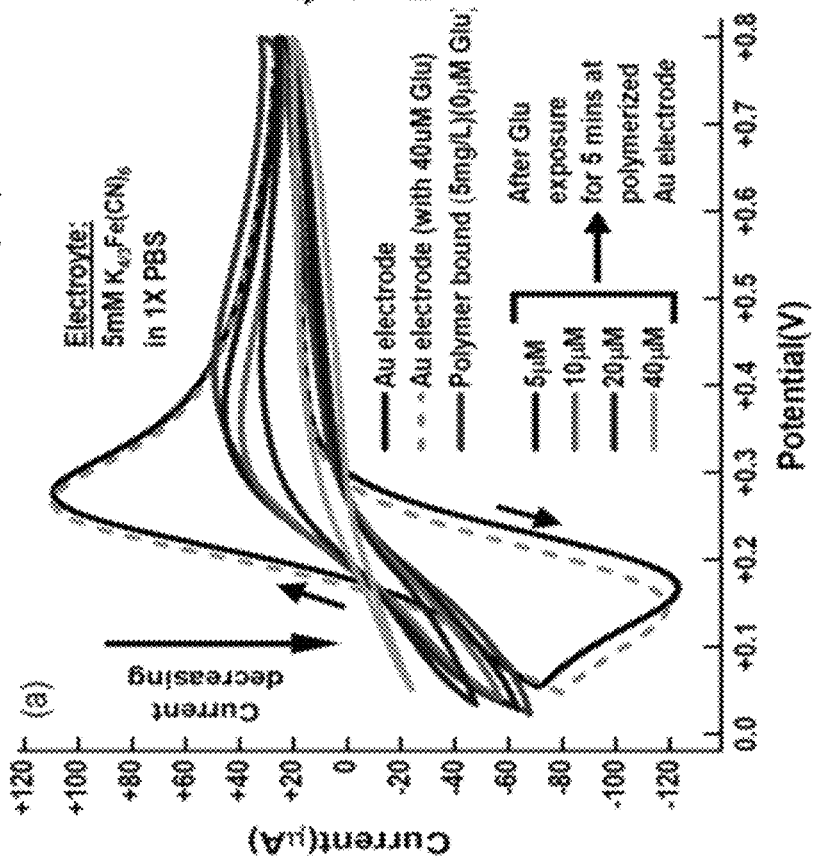
FIG. 7(b) shows a change in $R_{ct}$ after circuit fitting of a Nyquist plot with circuit parameters $R_s$ (solution resistance), Q (non-ideal capacitor due to frequency dispersion), $R_{ct}$ (resistance for charge transfer) and W (Warburg element for diffusion), in accordance with embodiments of the present disclosure. A modified Randles circuit is shown in the inset.

The CV curves in FIG. 7(a) show that bare Au electrode before and after exposure to Glu have similar electrode kinetics, suggesting that Glu is not readily adsorbed on the gold surface. Binding of Glu to the polymer decreases the intensity of redox peaks, which further decreases the rate constants. Also, the Nyquist plot obtained from EIS shows an increase in charge transfer resistance upon analyte binding. The circuit fitting in FIG. 7(b) shows that, upon binding of Glu, the charge transfer is more kinetically controlled, indicating more surface blockage upon Glu binding. The circuit fitting parameters summarized in Table 2 shows that, as more Glu are bound to the polymers, it not only increases the $R_{ct}$ but also increases the Warburg coefficient ($A_w$) obtained from Warburg element (W) fitting (A. J. Bard and L. R. Faulkner, *Electrochemical Methods: Fundamentals and Applications, 2nd Edition*). The increasing value of $A_w$, also suggests that the diffusion of electrolyte through the polymer is hindered upon gradual binding of Glu.

TABLE 2

EIS circuit fitting parameters obtained before and after Glu exposure to the templated polymer-based sensor.
Circuit Parameters
Polymer coated gold electrode with and without Glutamate binding

| Samples | Electrolyte Resistance $R_s$ (Ω) | Electrode-Polymer Interface | | | Aw (Ω. s$^{-0.5}$) |
|---|---|---|---|---|---|
| | | $Q_1$ (μF. s$^{n-1}$) | $n_1$ | $R_{ct}$ (Ω) | |
| Gold | 84.3 ± 0.2 | 10 ± 3 | 0.87 ± 0.5 | 40.6 ± 1.2 | 440 ± 1 |
| 0 μM-Gla | 97.9 ± 0.2 | 10.4 ± 0.3 | 0.84 ± 0.5 | 351 ± 0.9 | 456 ± 3 |
| 5 μM-Glu | 95.2 ± 0.2 | 8.5 ± 0.1 | 0.88 ± 0.5 | 661 ± 0.5 | 502 ± 3 |
| 10 μM-Glu | 97.4 ± 0.2 | 9.5 ± 0.1 | 0.85 ± 0.5 | 824.3 ± 0.8 | 598 ± 2 |
| 20 μM-Glu | 95.9 ± 0.2 | 7.2 ± 0.5 | 0 85 ± 0.5 | 1219 ± 1 | 632 ± 3 |
| 40 μM-Glu | 97.5 ± 0.2 | 10.1 ± 0.2 | 0.85 ± 0.5 | 3162 ± 6 | 1064 ± 7 |

Figure 8A:
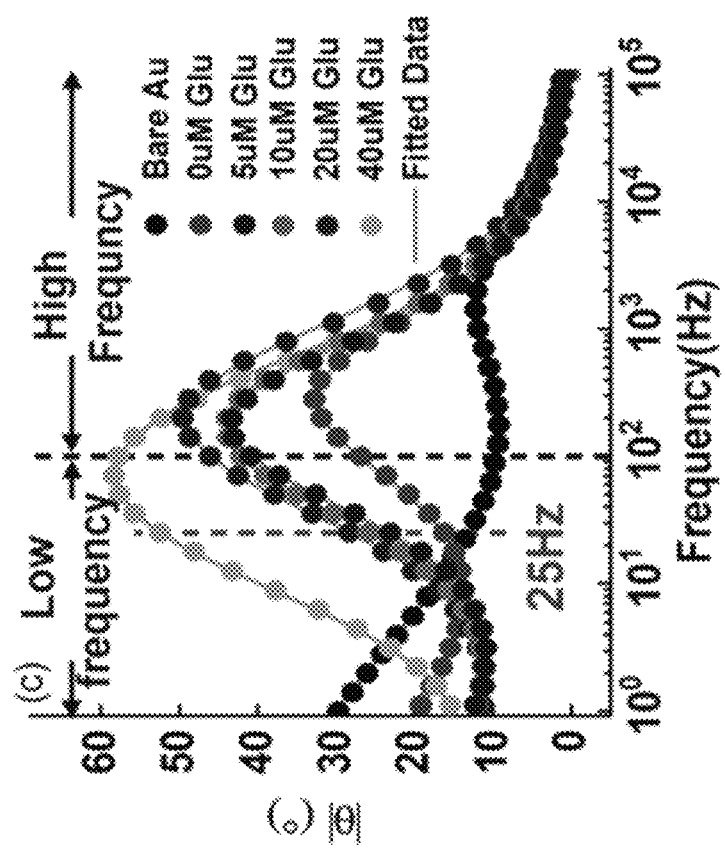
FIG. 8(a) shows corresponding change in impedance for various concentrations of Glu binding derived from a Bode plot under impedance spectra, in accordance with embodiments of the present disclosure.
Figure 8B:
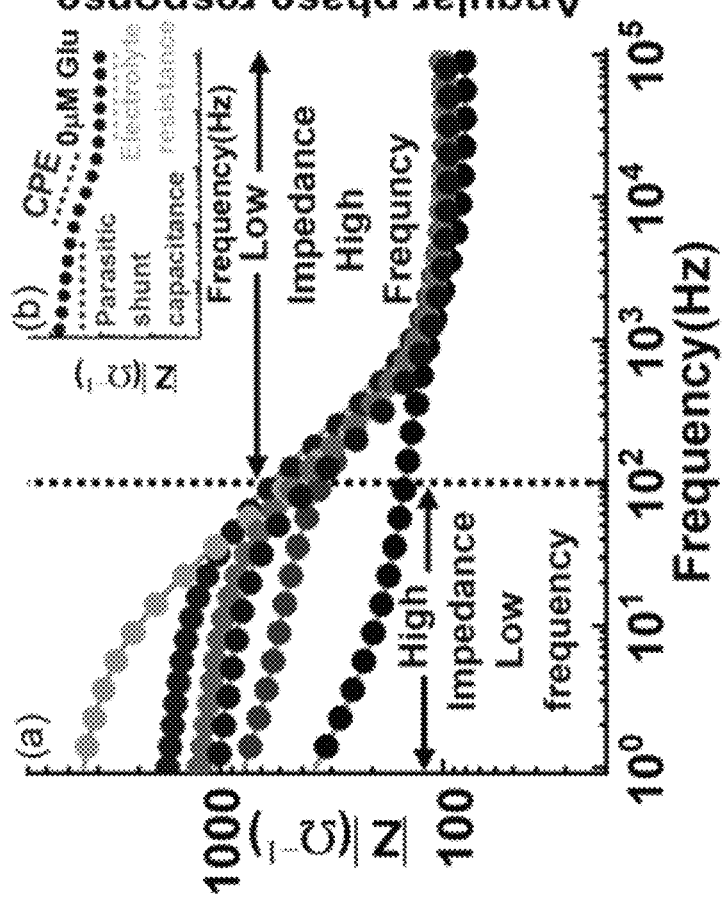
FIG. 8(b) is change in phase plot for different concentrations of Glu binding with respect to 0 μM Glu, in accordance with embodiments of the present disclosure.
Figure 9A:
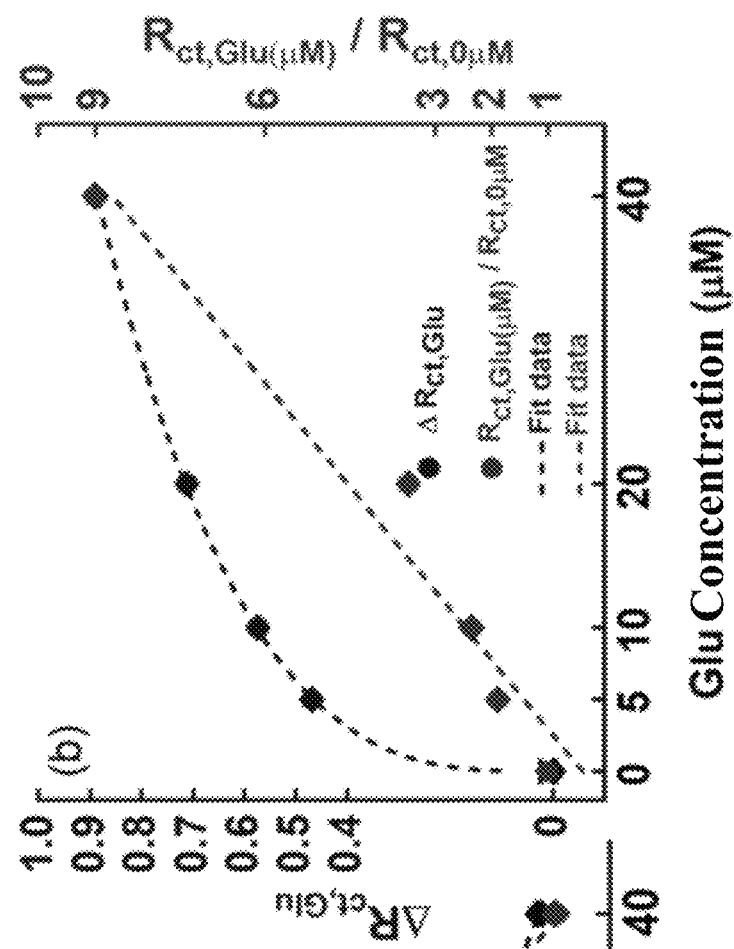
FIG. 9(a) shows changes in rate constant under various concentrations of Glu binding obtained from CV and EIS measurements, in accordance with embodiments of the present disclosure.
Figure 9B:
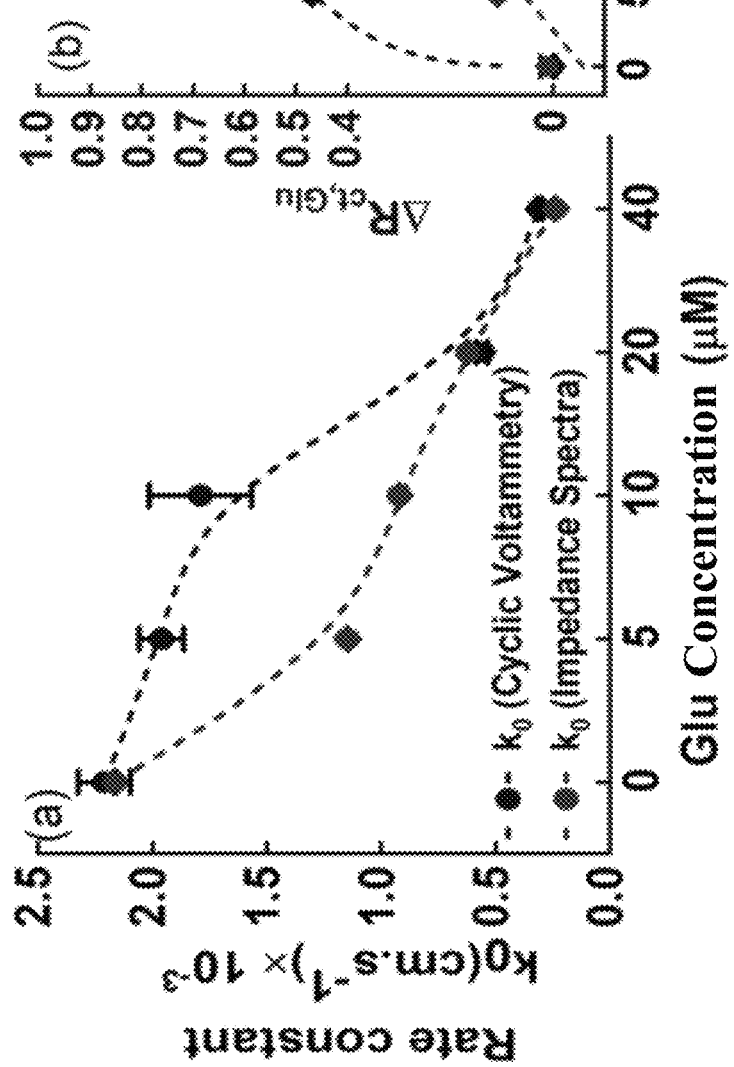
FIG. 9(b) shows percentage change in $R_{ct}$ and the ratio of $R_{ct}$ before and after Glu binding, in accordance with embodiments of the present disclosure.

FIGS. 8(a) and 8(b) show a Bode magnitude and phase plot, respectively. The bare Au electrode shows parasitic shunt capacitance at Z<100 Hz due to the exposed metal surface resulting in enhanced charge transfer at a lower frequency range. The lower frequency domain at the Bode plot shows decreased shunt capacitance upon polymer attachment and further binding of higher concentrations of Glu to the polymers. The conformation change of the polymers is confirmed by a decrease in the parasitic leakage pathway. This is observed by a rising impedance due to the passivation of the metal surface via the polymer deposition and subsequent Glu binding. The phase plot in FIG. 8(b) shows that the peak phase response shifts toward the lower frequency upon binding of polymer and Glu (M. M. Straka, B. Shafer, S. Vasudevan, C. Welle, and L. Rieth, "Characterizing Longitudinal Changes in the Impedance Spectra of In-Vivo Peripheral Nerve Electrodes," *Micromachines*, vol. 9, no. 11, p. 587, November 2018). At the lower frequency domain (f<100 Hz), the phase differences among the responses are maximized at 25 Hz (C. Tan, G. Dutta, H. Yin, S. Siddiqui, and P. U. Arumugam, "Detection of neurochemicals with enhanced sensitivity and selectivity via hybrid multiwall carbon nanotube-ultrananocrystalline diamond microelectrodes,"*Sens. Actuators B Chem.*, vol. 258, pp. 193-203, April 2018). FIG. 9(a) shows the change in rate kinetics before and after binding of Glu. The rate constant ($k_0$) values are obtained from CV and EIS by equations (2) and (3) by Kochi and Klinger, respectively (A. J. Bard and L. R. Faulkner, *Electrochemical Methods: Fundamentals and Applications, 2nd Edition*; V. Ganesh, S. K. Pal, S. Kumar, and V. Lakshminarayanan, "Self-assembled monolayers (SAMs) of alkoxycyanobiphenyl thiols on gold—A study of electron transfer reaction using cyclic voltammetry and electrochemical impedance spectroscopy," *J. Colloid Interface Sci.*, vol. 296, no. 1, pp. 195-203, April 2006):

$$K_0 = 2.18 \left[ \frac{\alpha D n F \vartheta}{RT} \right]^{-0.5} \times \exp\left[ \frac{-\alpha^2 n F (\Delta E_p)}{RT} \right] \quad \text{Equation (2)}$$

$$K_0 = \frac{R \cdot T}{n \cdot F^2 \cdot C \cdot A \cdot R_{ct}} \quad \text{Equation (3)}$$

where F=Faraday's constant (96,485 C/mol); A=electrode area (0.07 cm2); T=Temperature (298K); n=number of electrons=1; C=concentration (5 mM); $\vartheta$=scan rate (0.1 V/s); $\alpha$=transfer coefficient; $R_{ct}$=Charge transfer resistance from Nyquist plot. The $K_0$ value obtained from EIS [FIG. 9(a)] is significantly lower than that from CV [FIG. 9(b)] because of the electrochemical irreversibility at the electrode-electrolyte interface (E. P. Randviir, "A cross examination of electron transfer rate constants for carbon screen-printed electrodes using Electrochemical Impedance Spectroscopy and cyclic voltammetry," *Electrochimica Acta*, vol. 286, pp. 179-186, October 2018). The increase in Faradaic impedance after Glu binding shows an almost linear trend in FIG. 9(b). A nine-fold increase in $R_{ct}$ ratio indicates the specific binding of Glu (K. R. Rogers, "Principles of affinity-based biosensors," *Mol. Biotechnol.*, vol. 14, no. 2, pp. 109-129, February 2000). The $\Delta R_{ct}$ increment of approximately 90% was achieved at the highest Glu concentration. The exponential increment in $\Delta R_{ct}$ suggests an association of Glu molecule in polymer chain results in a globule (collapsed) conformation of polymers (V. Ganesh, S. K. Pal, S. Kumar, and V. Lakshminarayanan, "Self-assembled monolayers (SAMs) of alkoxycyanobiphenyl thiols on gold—A study of electron transfer reaction using cyclic voltammetry and electrochemical impedance spectroscopy," *J. Colloid Interface Sci.*, vol. 296, no. 1, pp. 195-203, April 2006).

Figure 10:
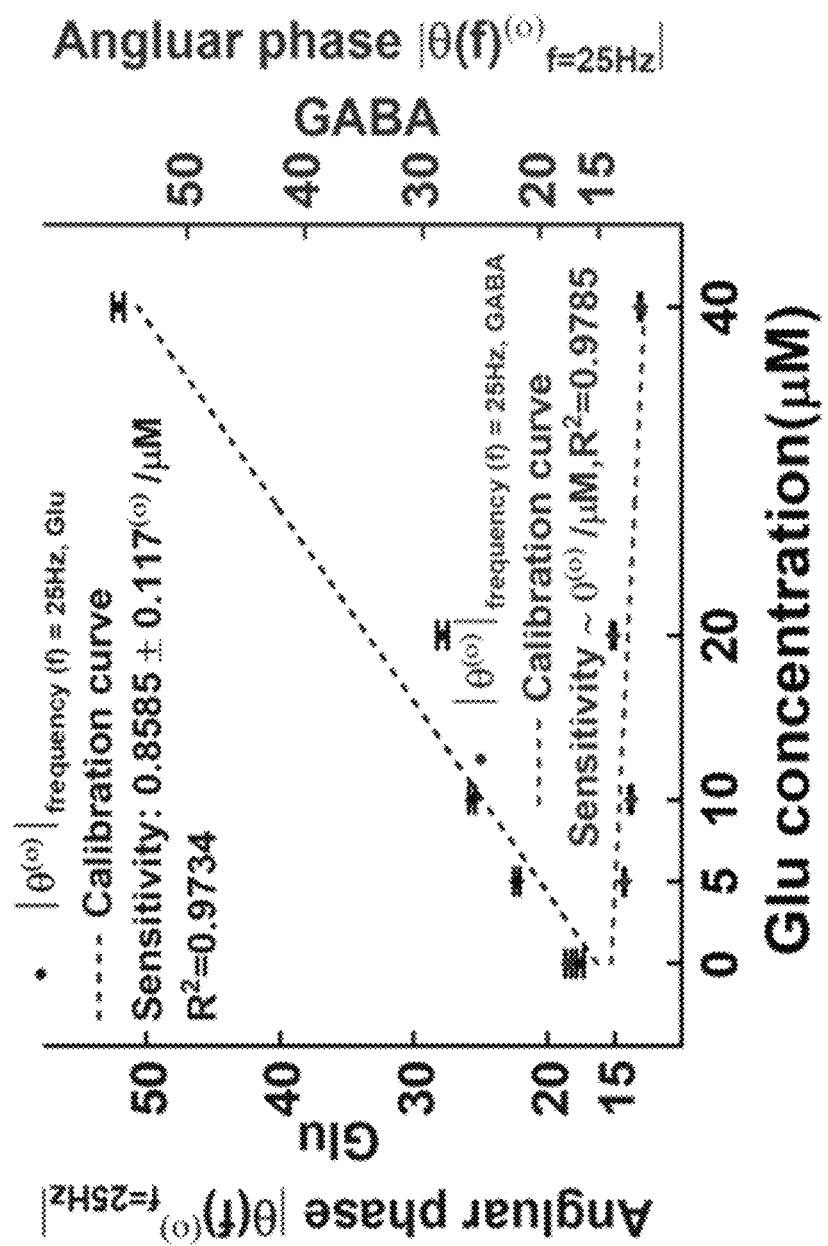
FIG. 10 is a calibration curve showing angular phase vs. concentration, in accordance with embodiments of the present disclosure. The changes in angular phase were measured before and after binding of various concentrations of Glu (upper line) and gammaaminobutyric acid (GABA) (lower line) at 25 Hz.

The angular phase displacement (θ) obtained from EIS in FIG. 10 depicts the impediment in diffusion through the porous network of the polymer due to the binding of Glu. The conformational change (from a random coil (extended) conformation to a globule (collapsed) conformation) of the single-chain templated polymer contributes towards change in phase. The maximum angular phase obtained from the phase plot at 25 Hz in the lower frequency domain (<100 Hz) has proportionally increased upon Glu binding. The slope calculated from the phase graph shows the sensitivity of the disclosed polymer-based Glu sensor, which is 0.86±0.12°/µM. The limit of detection (LOD) for Glu detection is calculated to be 1.7±0.2 µM. The selectivity of the templated polymer is assessed by exposing the Glu-templated polymer to gammaaminobutyric acid (GABA), another neurochemical. The phase response under GABA exposure yields a straight line with negligible slope. The comparison in the calibration curve between Glu and GABA in FIG. 10 demonstrates the selective nature of the template polymers.

Conclusion

Methyl-Glu templated polymer was developed for the selective electrochemical detection of Glu. The synthesized polymer has demonstrated a specific affinity towards Glu. Moreover, upon specific binding with Glu, the templated polymer undergoes conformation change from the extended to the collapsed state. The detection limit obtained for Glu was ~1.7 µM with reasonable selectivity against another neurotransmitter, GABA.

Although the present disclosure provides embodiments of 2-dimensional surfaces and methods of their use, one skilled in the art will appreciate that other types of 2-dimensional surfaces may be configured to implement the teachings herein. If non-electrochemical sensors are used, non-electrochemical sensing techniques may be used. Numerous such techniques are known in the art and include, but are not limited to, optical techniques, fluorescent techniques, surface plasmon resonance, and others.

Although the present disclosure has been particularly described in conjunction with specific embodiments, it is evident that many alternatives, modifications, and variations will be apparent to those skilled in the art in light of the foregoing description. It is therefore contemplated that the appended claims will embrace any such alternatives, modifications, and variations as falling within the true spirit and scope of the present disclosure.

What is claimed is:

1. A method of generating an electrochemical sensor, comprising:
    obtaining a single-chain polymer comprising a carboxylic acid monomer, a monomer comprising a derivative of pyridine with a vinyl group, an organometallic compound, a monomer comprising a reversible addition-fragmentation chain transfer (RAFT) agent, and a backbone compound;
    generating a modified single-chain polymer by changing the RAFT agent to a thiol; and
    covalently linking the thiol to a sensor surface.

2. The method of claim 1, wherein the generating comprises producing a solution by dissolving the single-chain polymer in a liquid with a reducing agent.

3. The method of claim 2, wherein the liquid comprises water.

4. The method of claim 3, wherein the water comprises deionized water.

5. The method of claim 2, wherein the reducing agent comprises tris (2-carboxyethyl) phosphine (TCEP).

6. The method of claim 2, wherein the covalently linking comprises contacting the sensor surface with the solution.

7. The method of claim 1, wherein the sensor surface comprises a metal.

8. The method of claim 7, wherein the metal comprises at least one of gold, carbon, platinum, silicon, silicon dioxide, and silver.

9. The method of claim 1, wherein the carboxylic acid comprises methacrylic acid (MAA).

10. The method of claim 1, wherein the derivative of pyridine with the vinyl group comprises 4-vinylpyridine (4-VP).

11. The method of claim 1, wherein the organometallic compound comprises a transition metal.

12. The method of claim 11, wherein the transition metal is iron.

13. The method of claim 1, wherein the organometallic compound comprises a vinyl group.

14. The method of claim 1, wherein the organometallic compound comprises vinylferrocene.

15. The method of claim 1, wherein the organometallic compound is a terminal monomer of the modified single-chain polymer.

16. The method of claim 1, wherein the backbone compound comprises N-isopropylacrylamide (NIPAM).

17. The method of claim 1, wherein the single-chain polymer comprises repeating sequences of the carboxylic acid monomer and the monomer comprising the derivative of pyridine with the vinyl group.

18. The method of claim 1, wherein the RAFT agent comprises 2-(Dodecyl-thiocarbonothioylthio)-2-methyl-propanioc acid (DDMAT).

19. The method of claim 1, wherein the RAFT agent is a terminal residue of the single-chain polymer.

\* \* \* \* \*

UNITED STATES PATENT AND TRADEMARK OFFICE
CERTIFICATE OF CORRECTION

| | |
|---|---|
| PATENT NO. | : 11,899,012 B2 |
| APPLICATION NO. | : 18/149131 |
| DATED | : February 13, 2024 |
| INVENTOR(S) | : Song et al. |

It is certified that error appears in the above-identified patent and that said Letters Patent is hereby corrected as shown below:

In the Specification

Column 1, Line 6 add the following government clause:
--GOVERNMENT FUNDED RESEARCH
This invention was made with government support under NIH grant no. P20 GM113131. The government has certain rights in the invention.--

Signed and Sealed this
Fifteenth Day of October, 2024

Katherine Kelly Vidal
*Director of the United States Patent and Trademark Office*